US012708272B2

(12) United States Patent
Perez Saaibi et al.

(10) Patent No.: US 12,708,272 B2
(45) Date of Patent: Aug. 18, 2026

(54) RECEIVER ARRAYS FOR PHOTOACOUSTIC DEVICES

(71) Applicant: QUALCOMM Incorporated, San Diego, CA (US)

(72) Inventors: Camilo Perez Saaibi, Dublin, CA (US); Hrishikesh Vijaykumar Panchawagh, Cupertino, CA (US); Sumit Agrawal, Sunnyvale, CA (US); Kostadin Dimitrov Djordjev, Los Gatos, CA (US)

(73) Assignee: QUALCOMM Incorporated, San Diego, CA (US)

( * ) Notice: Subject to any disclaimer, the term of this patent is extended or adjusted under 35 U.S.C. 154(b) by 169 days.

(21) Appl. No.: 18/323,021

(22) Filed: May 24, 2023

(65) Prior Publication Data

US 2024/0389860 A1 Nov. 28, 2024

(51) Int. Cl.
*A61B 5/00* (2006.01)
*A61B 5/02* (2006.01)
*A61B 5/021* (2006.01)

(52) U.S. Cl.
CPC ........ *A61B 5/0095* (2013.01); *A61B 5/02007* (2013.01); *A61B 5/021* (2013.01); *A61B 2562/043* (2013.01)

(58) Field of Classification Search
CPC ............ A61B 2562/043; A61B 5/0095; A61B 5/02007; A61B 5/021; A61B 5/02116; A61B 5/02125; A61B 5/0285; A61B 5/489
See application file for complete search history.

(56) References Cited

U.S. PATENT DOCUMENTS

2011/0208035 A1* 8/2011 Baba ........................ A61B 8/56 600/407
2015/0101411 A1* 4/2015 Zalev .................. A61B 5/0095 73/643
2017/0231578 A1* 8/2017 Lading ................ A61B 5/0261 600/473

(Continued)

OTHER PUBLICATIONS

Dr. Joseph Woo, “A short History of the development of Ultrasound in Obstetrics and Gynecology” (Year: 1998).*

(Continued)

*Primary Examiner* — Michael J Carey
*Assistant Examiner* — Maria Christina Talty
(74) *Attorney, Agent, or Firm* — QUALCOMM Incorporated

(57) ABSTRACT

Some disclosed examples involve controlling, by a control system, a light source system to provide light to a target object on an outer surface of a platen and receiving, by the control system, ultrasonic receiver signals from each of a plurality of ultrasonic receiver elements in an array of ultrasonic receiver elements. The ultrasonic receiver signals may correspond to ultrasonic waves generated by the target object responsive to the light from the light source system. Some disclosed examples involve applying, by the control system, a receiver-side beamforming process to the ultrasonic receiver signals, to produce a beamformed ultrasonic receiver image and detecting, by the control system, a blood vessel within the targe object based, at least in part, on the beamformed ultrasonic receiver image.

30 Claims, 17 Drawing Sheets

(56) References Cited

U.S. PATENT DOCUMENTS

| | | | | |
|---|---|---|---|---|
| 2022/0175258 | A1* | 6/2022 | Kitchens ............ | A61B 5/02116 |
| 2022/0175340 | A1 | 6/2022 | Xu et al. | |
| 2023/0130494 | A1* | 4/2023 | Kwon .................. | A61B 8/5207<br>340/304 |
| 2023/0363711 | A1* | 11/2023 | Theodore ............. | A61B 5/0031 |

OTHER PUBLICATIONS

International Search Report and Written Opinion—PCT/US2024/023914—ISA/EPO—Jun. 26, 2024.

* cited by examiner 225f
705
z
x
100
101
710
101a
101b
104
1 2 3 4 5 6
215
102, 202

RECEIVER ARRAYS FOR PHOTOACOUSTIC DEVICES

TECHNICAL FIELD

This disclosure relates generally to photoacoustic devices and more specifically to receiver arrays for photoacoustic devices.

DESCRIPTION OF RELATED TECHNOLOGY

A variety of different sensing technologies and algorithms are being implemented in devices for various biometric and biomedical applications, including health and wellness monitoring. This push is partly a result of the limitations in the usability of traditional measuring devices for continuous, noninvasive and ambulatory monitoring. Some such devices are, or include, photoacoustic devices. Although some previously-deployed photoacoustic devices and systems can provide acceptable results, improved photoacoustic devices and systems would be desirable.

SUMMARY

The systems, methods and devices of this disclosure each have several aspects, no single one of which is solely responsible for the desirable attributes disclosed herein.

One innovative aspect of the subject matter described in this disclosure can be implemented in an apparatus. In some implementations, a mobile device (such as a wearable device, a cellular telephone, etc.) may be, or may include, at least part of the apparatus. The apparatus may include a platen, a light source system and a receiver system. The light source system may be configured for providing light to a target object on an outer surface of the platen. In some examples, the light source system may include an array of light sources. The receiver system may be, or may include, an ultrasonic receiver system having an array of ultrasonic receiver elements. The ultrasonic receiver system may be configured to receive ultrasonic waves generated by the target object responsive to the light from the light source system.

In some implementations, the apparatus may include a control system. The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system may be configured to receive ultrasonic receiver signals from each of a plurality of ultrasonic receiver elements in the array. The ultrasonic receiver signals may correspond to ultrasonic waves generated by the target object responsive to the light from the light source system. According to some examples, the control system may be configured to apply a receiver-side beamforming process to the ultrasonic receiver signals, to produce a beamformed ultrasonic receiver image. In some such examples, the receiver-side beamforming process may be, or may include, a delay-and-sum beamforming process. In some examples, the control system may be configured to detect a blood vessel within the targe object based, at least in part, on the beamformed ultrasonic receiver image.

According to some examples, the control system may be configured to detect the blood vessel within the targe object based, at least in part, on the ultrasonic receiver signals. In some examples, the control system may be further configured to estimate one or more blood vessel features based, at least in part, on the beamformed ultrasonic receiver image. According to some examples, the one or more blood vessel features may include blood vessel diameter, blood vessel area, blood vessel profile, blood vessel distention, volumetric flow, pulse wave velocity, blood vessel wall thickness, or combinations thereof. In some examples, the control system may be further configured to estimate blood pressure based, at least in part, on the one or more blood vessel features.

In some examples, the apparatus may be configured to be worn by, or attached to, a person. According to some examples, the array of ultrasonic receiver elements may include a linear array of ultrasonic receiver elements arranged along an array axis that is configured to extend along the blood vessel and wherein the array axis is within plus or minus 45 degrees of a blood vessel axis. In some examples, the array of ultrasonic receiver elements may include a linear array of ultrasonic receiver elements arranged along an array axis that is configured to extend across the blood vessel.

According to some examples, the array of ultrasonic receiver elements may include a linear array of ultrasonic receiver elements having a pitch between adjacent ultrasonic receiver elements that is equal to a wavelength corresponding to a peak frequency of ultrasonic waves generated by the target object responsive to the light from the light source system. In some examples, the array of ultrasonic receiver elements may include a phased array of ultrasonic receiver elements having a pitch between adjacent ultrasonic receiver elements that is equal to a multiple of a half wavelength corresponding to a peak frequency of ultrasonic waves generated by the target object responsive to the light from the light source system. According to some examples, the array of ultrasonic receiver elements may include a two-dimensional array of ultrasonic receiver elements.

In some examples, the array of ultrasonic receiver elements may include an array of electrodes arranged on a piezoelectric layer. In some such examples, the piezoelectric layer may include lead zirconate titanate (PZT) or a piezoelectric composite.

Other innovative aspects of the subject matter described in this disclosure can be implemented in a method. The method may involve controlling, by a control system, a light source system to provide light to a target object on an outer surface of a platen.

According to some examples, the method may involve receiving, by the control system, ultrasonic receiver signals from each of a plurality of ultrasonic receiver elements in an array of ultrasonic receiver elements. The ultrasonic receiver signals may correspond to ultrasonic waves generated by the target object responsive to the light from the light source system.

In some examples, the method may involve applying, by the control system, a receiver-side beamforming process to the ultrasonic receiver signals, to produce a beamformed ultrasonic receiver image. In some such examples, the receiver-side beamforming process may be, or may include, a delay-and-sum beamforming process.

According to some examples, the method may involve detecting, by the control system, a blood vessel within the targe object based, at least in part, on the beamformed ultrasonic receiver image. In some examples, the method may involve detecting the blood vessel within the target object based, at least in part, on the ultrasonic receiver signals. According to some examples, the method may involve estimating one or more blood vessel features based, at least in part, on the beamformed ultrasonic receiver image.

According to some examples, the one or more blood vessel features may include blood vessel diameter, blood vessel area, blood vessel profile, blood vessel distention, volumetric flow, pulse wave velocity, blood vessel wall thickness, or combinations thereof. In some examples, the method may involve estimating blood pressure based, at least in part, on the one or more blood vessel features.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in one or more non-transitory media having software stored thereon. The software may include instructions for controlling one or more devices to perform one or more disclosed methods.

According to some examples, the method may involve receiving, by the control system, ultrasonic receiver signals from each of a plurality of ultrasonic receiver elements in an array of ultrasonic receiver elements. The ultrasonic receiver signals may correspond to ultrasonic waves generated by the target object responsive to the light from the light source system.

In some examples, the method may involve applying, by the control system, a receiver-side beamforming process to the ultrasonic receiver signals, to produce a beamformed ultrasonic receiver image. In some such examples, the receiver-side beamforming process may be, or may include, a delay-and-sum beamforming process.

According to some examples, the method may involve detecting, by the control system, a blood vessel within the targe object based, at least in part, on the beamformed ultrasonic receiver image. In some examples, the method may involve detecting the blood vessel within the target object based, at least in part, on the ultrasonic receiver signals. According to some examples, the method may involve estimating one or more blood vessel features based, at least in part, on the beamformed ultrasonic receiver image.

According to some examples, the one or more blood vessel features may include blood vessel diameter, blood vessel area, blood vessel profile, blood vessel distention, volumetric flow, pulse wave velocity, blood vessel wall thickness, or combinations thereof. In some examples, the method may involve estimating blood pressure based, at least in part, on the one or more blood vessel features.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

Like reference numbers and designations in the various drawings indicate like elements.

DETAILED DESCRIPTION

Figure 1:
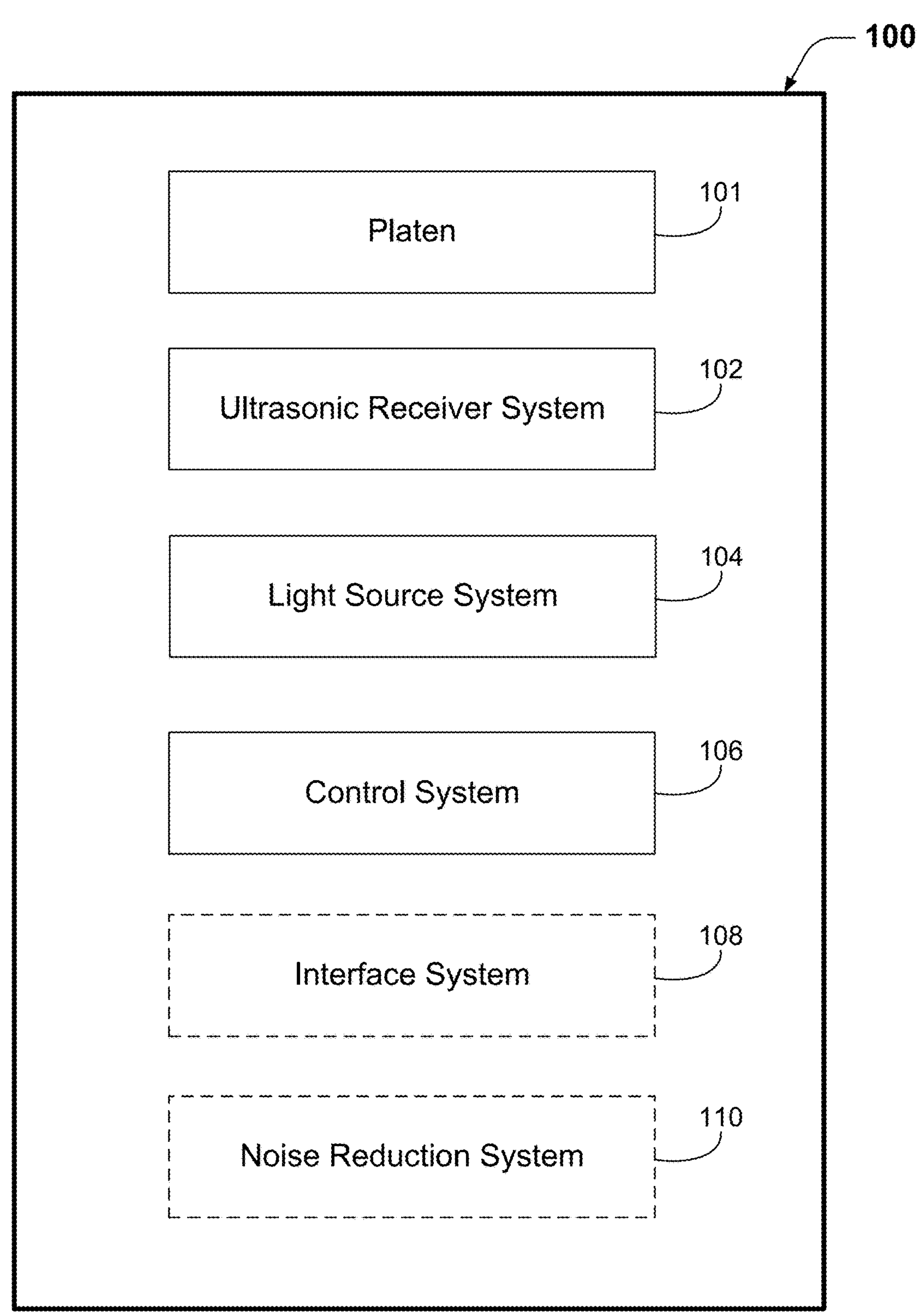
FIG. 1 is a block diagram that shows example components of an apparatus according to some disclosed implementations.

The following description is directed to certain implementations for the purposes of describing various aspects of this disclosure. However, a person having ordinary skill in the art will readily recognize that the teachings herein can be applied in a multitude of different ways. Some of the concepts and examples provided in this disclosure are especially applicable to blood pressure monitoring applications. However, some implementations also may be applicable to other types of biological sensing applications, as well as to other fluid flow systems. The described implementations may be implemented in any device, apparatus, or system that includes an apparatus as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, handheld or portable computers, netbooks, notebooks, smartbooks, tablets, printers, copiers, scanners, facsimile devices, global positioning system (GPS) receivers/navigators, cameras, digital media players, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), architectural structures, microwaves, refrigerators, stereo systems, cassette recorders or players, digital video disc (DVD™) players, compact disc (CD) players, videocassette recorders (VCRs), radios, portable memory chips, washers, dryers, washer/dryers, parking meters, automobile doors, autonomous or semi-autonomous vehicles, drones, Internet of Things (IoT) devices, etc. Thus, the teachings are not intended to be limited to the specific implementations depicted and described with reference to the drawings; rather, the teachings have wide applicability as will be readily apparent to persons having ordinary skill in the art.

Non-invasive health monitoring devices, such as photoacoustic plethysmography (PAPG)-capable devices, have various potential advantages over more invasive health monitoring devices such as cuff-based or catheter-based blood pressure measurement devices. However, it has proven to be difficult to design satisfactory PAPG-based devices. One challenge is that the signal-to-noise ratio (SNR) for signals of interest, such as signals corresponding to ultrasound caused by the photoacoustic response of arterial walls, is low. For example, the signals corresponding to arterial walls are generally significantly lower in amplitude than signals corresponding to the photoacoustic response of skin. Another challenge is that the orientation of the same artery may vary from user to user and within the body of the same user. These variations in arterial orientation can make it challenging to properly position the ultrasonic receiver of a PAPG-based device. Small changes in the ultrasonic receiver position may result in significant differences in the received signals corresponding to arterial walls.

Some disclosed devices include a platen, a light source system, an ultrasonic receiver system and a control system. According to some implementations, the light source system may be configured for providing light to a target object on an outer surface of the platen. The ultrasonic receiver system may be configured to receive ultrasonic waves generated by the target object responsive to the light from the light source system. The ultrasonic receiver system may include an array of ultrasonic receiver elements. According to some implementations, the control system may be configured to apply a receiver-side beamforming process to ultrasonic receiver signals received from each of a plurality of ultrasonic receiver elements in the array. In some implementations, the control system may be configured to detect a blood vessel within the targe object based, at least in part, on the beamformed ultrasonic receiver image. According to some implementations, the control system may be configured to estimate one or more blood vessel features based, at least in part, on the beamformed ultrasonic receiver image. In some implementations, the control system may be configured to estimate blood pressure based, at least in part, on the one or more blood vessel features.

Particular implementations of the subject matter described in this disclosure can be implemented to realize one or more of the following potential advantages. Various disclosed configurations include PAPG-capable devices that can provide a higher SNR—as compared to previously-deployed devices having a single receiver element—for signals corresponding to the photoacoustic response of one or more arterial walls. Signals obtained from multiple receiver elements of an ultrasonic receiver array can provide information about the position of an artery that would not be available if signals were obtained from only a single ultrasonic receiver element. Signals obtained from multiple receiver elements of an ultrasonic receiver array can provide information regarding a local pulse wave velocity, which can provide information regarding arterial hemodynamics, localized blood vessel stiffening, etc. Having an array of ultrasonic receiver elements can provide a greater tolerance for misalignment of the ultrasonic receiver system, as compared to ultrasonic receiver systems having a single receiver element.

FIG. 1 is a block diagram that shows example components of an apparatus according to some disclosed implementations. In this example, the apparatus 100 includes a platen 101, an ultrasonic receiver system 102, a control system 106 and a light source system 104. Some implementations of the apparatus 100 may include an interface system 108, a noise reduction system 110, or both. As with other disclosed implementations, in some alternative implementations the apparatus 100 may include more components, fewer components or different components.

In some implementations, the platen 101 may be configured to increase an intensity of ultrasonic energy received by at least a portion of the ultrasonic receiver system. In some such implementations, the platen 101 may include an acoustic waveguide. According to some implementations, the platen 101 may include an acoustic lens system. The acoustic lens system may, for example, reside on, or proximate, an outer surface of the platen 101. The acoustic lens system may, for example, include a spherical lens or a cylindrical lens.

According to some examples, the platen 101, the light source system 104, or a combination thereof, may be configured for transmitting at least some of the light from the light source system to an outer surface of the platen (or to a target object on, or proximate, the outer surface) along a first axis, or substantially along the first axis oriented at a first angle relative to the outer surface of the platen. In this context, "substantially along the first axis" may mean within an angle range of plus or minus 10 degrees of the first axis, within an angle range of plus or minus 15 degrees of the first axis, within an angle range of plus or minus 20 degrees of the first axis, within an angle range of plus or minus 25 degrees of the first axis, within an angle range of plus or minus 30 degrees of the first axis, or within another such angle range.

In some examples, at least a portion of the platen 101 may be configured for transmitting at least some of the ultrasonic waves generated by the target object along a third axis, or substantially along the third axis, that is at a third angle relative to the outer surface of the platen. According to some examples, the third axis may be parallel to the second axis.

According to some examples, the platen 101 may include different portions, which may have varying thicknesses, orientations, etc., depending on the particular implementation. In some examples, the platen 101 may include a first platen portion residing between the light source system and the outer surface of the platen. In some examples, the first platen portion may have a first platen portion thickness that is less than a second platen portion thickness of a second platen portion residing between at least one receiver element of the ultrasonic receiver system 102 and the outer surface of the platen. In some such examples, the first platen portion may be configured to receive light from the light source system and may also be configured to reflect the ultrasonic waves generated by the target object towards at least one receiver element of the receiver system. However, in some examples, a first platen portion residing between the light source system and the outer surface of the platen may have a first platen portion thickness that is greater than a second platen portion residing between at least one receiver element of the ultrasonic receiver system 102 and the outer surface of the platen.

According to some examples, the platen 101 (or another portion of the apparatus) may include one or more anti-reflective layers. In some examples, one or more anti-reflective layers may reside on, or proximate, one or more outer surfaces of the platen 101.

In some examples, at least a portion of the outer surface of the platen 101 may have an acoustic impedance that is configured to approximate an acoustic impedance of human skin. The portion of the outer surface of the platen 101 may, for example, be a portion that is configured to receive a target object, such as a human digit. (As used herein, the terms "finger" and "digit" may be used interchangeably, such that a thumb is one example of a finger.) A typical range of acoustic impedances for human skin is 1.53-1.680 MRayls. In some examples, at least an outer surface of the platen 101 may have an acoustic impedance that is in the range of 1.4-1.8 MRayls, or in the range of 1.5-1.7 MRayls.

Alternatively, or additionally, in some examples at least an outer surface of the platen 101 may be configured to conform to a surface of human skin. In some such examples, at least an outer surface of the platen 101 may have material properties like those of putty or chewing gum.

In some examples, at least a portion of the platen 101 may have an acoustic impedance that is configured to approximate an acoustic impedance of one or more receiver elements of the ultrasonic receiver system 102. According to some examples, a layer residing between the platen 101 and one or more receiver elements may have an acoustic impedance that is configured to approximate an acoustic impedance of the one or more receiver elements. Alternatively, or additionally, in some examples a layer residing between the platen 101 and one or more receiver elements may have an acoustic impedance that is in an acoustic impedance range between an acoustic impedance of the platen and an acoustic impedance of the one or more receiver elements.

In this example, the ultrasonic receiver system 102 includes an array of ultrasonic receiver elements. Various examples and configurations of ultrasonic receiver systems 102 are disclosed herein. According to some examples, the array of ultrasonic receiver elements may be a linear array. In other examples, the array of ultrasonic receiver elements may be a two-dimensional array. According to some examples, a linear or a two-dimensional array of ultrasonic receiver elements may be arranged in a plane, whereas in other examples, a linear or a two-dimensional array of ultrasonic receiver elements may be arranged along a non-planar surface, such as a curved surface. In some examples, a linear or a two-dimensional array of ultrasonic receiver elements may be a phased array, in which there is a phase difference between samples from adjacent ultrasonic receiver elements. Some examples are described in more detail below. In some examples, the ultrasonic receiver system 102 may include an array of electrodes arranged on a piezoelectric receiver layer, such as a layer of PVDF polymer, a layer of PVDF-TrFE copolymer, or a layer of piezoelectric composite material. In some implementations, other piezoelectric materials may be used in the piezoelectric layer, such as aluminum nitride (AlN) or lead zirconate titanate (PZT).

In some examples, the apparatus 100 may be configured for transmitting as well as receiving ultrasound. The ultrasonic receiver system 102 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, a piezoelectric receiver layer, PMUT elements in a single-layer array of PMUTs, or CMUT elements in a single-layer array of CMUTs, may be used as ultrasonic transmitters as well as ultrasonic receivers. According to some examples, the ultrasonic receiver system 102 may be, or may include, an ultrasonic receiver array. In some examples, the apparatus 100 may include one or more separate ultrasonic transmitter elements. In some such examples, the ultrasonic transmitter (s) may include an ultrasonic plane-wave generator. However, in some examples the same layer, for example a single piezoelectric layer, may be configured to transmit as well as to receive ultrasound. According to some examples, an array of electrodes may reside on the same piezoelectric layer. In some such examples, the array of electrodes and the piezoelectric layer may function as both an ultrasonic transmitter array and an ultrasonic receiver array. Accordingly, in some examples the ultrasonic receiver system 102 also may function as an ultrasonic transmitter system.

According to some examples, the ultrasonic receiver system 102 may include an array of ultrasonic receiver elements residing in a receiver plane. In some examples, the normal to the receiver plane may be oriented along a second axis, or substantially along the second axis, at a second angle relative to the outer surface of the platen. In this context, "substantially along the second axis" may mean within an angle range of plus or minus 10 degrees of the second axis, within an angle range of plus or minus 15 degrees of the second axis, within an angle range of plus or minus 20 degrees of the second axis, within an angle range of plus or minus 25 degrees of the second axis, within an angle range of plus or minus 30 degrees of the second axis, or within another such angle range. According to some examples, the second axis may be parallel to the first axis. However, in some examples, the second angle may be different from the first angle.

According to some implementations, the light source system 104 may include one or more light-emitting diodes (LEDs). In some implementations, the light source system 104 may include one or more laser diodes. According to some implementations, the light source system 104 may include one or more vertical-cavity surface-emitting lasers (VCSELs). In some implementations, the light source system 104 may include one or more edge-emitting lasers. In some implementations, the light source system may include one or more neodymium-doped yttrium aluminum garnet (Nd:YAG) lasers. The light source system 104 may, in some examples, include an array of light-emitting elements, such as an array of LEDs, an array of laser diodes, an array of VCSELs, an array of edge-emitting lasers, or combinations thereof.

According to some examples, the light source system 104 may include one or more light-directing elements configured to direct light from the light source system towards the target object along the first axis. In some examples, the one or more light-directing elements may include at least one diffraction grating. Alternatively, or additionally, the one or more light-directing elements may include at least one lens.

The light source system 104 may, in some examples, be configured to transmit light in one or more wavelength ranges. In some examples, the light source system 104 may configured for transmitting light in a wavelength range of 500 to 600 nanometers. According to some examples, the light source system 104 may configured for transmitting light in a wavelength range of 800 to 950 nanometers.

The light source system 104 may include various types of drive circuitry, depending on the particular implementation. In some disclosed implementations, the light source system 104 may include at least one multi-junction laser diode, which may produce less noise than single-junction laser diodes. In some examples, the light source system 104 may include a drive circuit (also referred to herein as drive circuitry) configured to cause the light source system to emit pulses of light at pulse widths in a range from 3 nanoseconds to 1000 nanoseconds. According to some examples, the light source system 104 may include a drive circuit configured to cause the light source system to emit pulses of light at pulse repetition frequencies in a range from 1 kilohertz to 100 kilohertz.

In some examples, the light source system 104 may include a light source system surface having a normal that is parallel, or substantially parallel, to the first axis. In some such examples, a light source of the light source system may reside on, or proximate, the light source system surface.

In some implementations, the light source system 104 may be configured for emitting various wavelengths of light, which may be selectable to trigger acoustic wave emissions primarily from a particular type of material. For example, because the hemoglobin in blood absorbs near-infrared light very strongly, in some implementations the light source system 104 may be configured for emitting one or more wavelengths of light in the near-infrared range, in order to trigger acoustic wave emissions from hemoglobin. However, in some examples the control system 106 may control the wavelength(s) of light emitted by the light source system 104 to preferentially induce acoustic waves in blood vessels, other soft tissue, and/or bones. For example, an infrared (IR) light-emitting diode LED may be selected and a short pulse of IR light emitted to illuminate a portion of a target object and generate acoustic wave emissions that are then detected by the ultrasonic receiver system 102. In another example, an IR LED and a red LED or other color such as green, blue, white or ultraviolet (UV) may be selected and a short pulse of light emitted from each light source in turn with ultrasonic images obtained after light has been emitted from each light source. In other implementations, one or more light sources of different wavelengths may be fired in turn or simultaneously to generate acoustic emissions that may be detected by the ultrasonic receiver. Image data from the ultrasonic receiver that is obtained with light sources of different wavelengths and at different depths (e.g., varying RGDs) into the target object may be combined to determine the location and type of material in the target object. Image contrast may occur as materials in the body generally absorb light at different wavelengths differently. As materials in the body absorb light at a specific wavelength, they may heat differentially and generate acoustic wave emissions with sufficiently short pulses of light having sufficient intensities. Depth contrast may be obtained with light of different wavelengths and/or intensities at each selected wavelength. That is, successive images may be obtained at a fixed RGD (which may correspond with a fixed depth into the target object) with varying light intensities and wavelengths to detect materials and their locations within a target object. For example, hemoglobin, blood glucose or blood oxygen within a blood vessel inside a target object such as a finger may be detected photoacoustically.

According to some implementations, the light source system 104 may be configured for emitting a light pulse with a pulse width less than about 100 nanoseconds. In some implementations, the light pulse may have a pulse width between about 10 nanoseconds and about 500 nanoseconds or more. According to some examples, the light source system may be configured for emitting a plurality of light pulses at a pulse repetition frequency between 10 Hz and 100 kHz. Alternatively, or additionally, in some implementations the light source system 104 may be configured for emitting a plurality of light pulses at a pulse repetition frequency between about 1 MHz and about 100 MHz. Alternatively, or additionally, in some implementations the light source system 104 may be configured for emitting a plurality of light pulses at a pulse repetition frequency between about 10 Hz and about 1 MHz. In some examples, the pulse repetition frequency of the light pulses may correspond to an acoustic resonant frequency of the ultrasonic receiver and the substrate. For example, a set of four or more light pulses may be emitted from the light source system 104 at a frequency that corresponds with the resonant frequency of a resonant acoustic cavity in the sensor stack, allowing a build-up of the received ultrasonic waves and a higher resultant signal strength. In some implementations, filtered light or light sources with specific wavelengths for detecting selected materials may be included with the light source system 104. In some implementations, the light source system may contain light sources such as red, green and blue LEDs of a display that may be augmented with light sources of other wavelengths (such as IR and/or UV) and with light sources of higher optical power. For example, high-power laser diodes or electronic flash units (e.g., an LED or xenon flash unit) with or without filters may be used for short-term illumination of the target object.

The control system 106 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 106 also may include (and/or be configured for communication with) one or more memory devices, such as one or more random access memory (RAM) devices, read-only memory (ROM) devices, etc. Accordingly, the apparatus 100 may have a memory system that includes one or more memory devices, though the memory system is not shown in FIG. 1. The control system 106 may be configured for receiving and processing data from the ultrasonic receiver system 102, e.g., as described below. If the apparatus 100 includes an ultrasonic transmitter, the control system 106 may be configured for controlling the ultrasonic transmitter. In some implementations, functionality of the control system 106 may be partitioned between one or more controllers or processors, such as a dedicated sensor controller and an applications processor of a mobile device.

In some examples, the control system 106 may be configured to control the light source system 104 to emit light towards a target object on an outer surface of the platen 101. In some such examples, the control system 106 may be configured to receive signals from each of a plurality of ultrasonic receiver elements in an array of ultrasonic receiver elements of the ultrasonic receiver system 102. The signals may correspond to the ultrasonic waves generated by the target object responsive to the light from the light source system 104. In some examples, the control system 106 may be configured to apply a receiver-side beamforming process to the ultrasonic receiver signals, to produce a beamformed ultrasonic receiver image. According to some examples, the control system 106 may be configured to detect a blood vessel within the targe object based, at least in part, on the beamformed ultrasonic receiver image. In some such examples, the control system 106 may be configured to estimate one or more blood vessel features based, at least in part, on the beamformed ultrasonic receiver image. In some examples, the control system 106 may be configured to estimate one or more cardiac features based, at least in part, on one or more arterial signals, on the blood vessel features. According to some examples, the cardiac features may be, or may include, blood pressure.

Alternatively, or additionally, in some examples the control system 106 may be configured to control the an ultrasonic transmitter to emit ultrasound towards a target object on an outer surface of the platen 101. In some such examples, the control system 106 may be configured to receive signals from each of a plurality of ultrasonic receiver elements in an array of ultrasonic receiver elements of the ultrasonic receiver system 102. The signals may correspond to the ultrasonic waves reflected by the target object responsive to transmitted ultrasound. In some examples, the control system 106 may be configured to apply a receiver-side beamforming process to the ultrasonic receiver signals, to produce a beamformed ultrasonic receiver image. According to some examples, the control system 106 may be configured to detect a blood vessel within the targe object based, at least in part, on the beamformed ultrasonic receiver image. In some such examples, the control system 106 may be configured to estimate one or more blood vessel features based, at least in part, on the beamformed ultrasonic receiver image. In some examples, the control system 106 may be configured to estimate one or more cardiac features based, at least in part, on one or more arterial signals, on the blood vessel features. According to some examples, the cardiac features may be, or may include, blood pressure.

Some implementations of the apparatus 100 may include the interface system 108. In some examples, the interface system 108 may include a wireless interface system. In some implementations, the interface system 108 may include a user interface system, one or more network interfaces, one or more interfaces between the control system 106 and a memory system and/or one or more interfaces between the control system 106 and one or more external device interfaces (e.g., ports or applications processors), or combinations thereof. According to some examples in which the interface system 108 is present and includes a user interface system, the user interface system may include a microphone system, a loudspeaker system, a haptic feedback system, a voice command system, one or more displays, or combinations thereof. According to some examples, the interface system 108 may include a touch sensor system, a gesture sensor system, or a combination thereof. The touch sensor system (if present) may be, or may include, a resistive touch sensor system, a surface capacitive touch sensor system, a projected capacitive touch sensor system, a surface acoustic wave touch sensor system, an infrared touch sensor system, any other suitable type of touch sensor system, or combinations thereof.

In some examples, the interface system 108 may include, a force sensor system. The force sensor system (if present) may be, or may include, a piezo-resistive sensor, a capacitive sensor, a thin film sensor (for example, a polymer-based thin film sensor), another type of suitable force sensor, or combinations thereof. If the force sensor system includes a piezo-resistive sensor, the piezo-resistive sensor may include silicon, metal, polysilicon, glass, or combinations thereof. An ultrasonic fingerprint sensor and a force sensor system may, in some implementations, be mechanically coupled. In some such examples, the force sensor system may be integrated into circuitry of the ultrasonic fingerprint sensor. In some examples, the interface system 108 may include an optical sensor system, one or more cameras, or a combination thereof.

According to some examples, the apparatus 100 may include a noise reduction system 110. For example, the noise reduction system 110 may include one or more mirrors that are configured to reflect light from the light source system 104 away from the ultrasonic receiver system 102. In some implementations, the noise reduction system 110 may include one or more sound-absorbing layers, acoustic isolation material, light-absorbing material, light-reflecting material, or combinations thereof. In some examples, the noise reduction system 110 may include acoustic isolation material, which may reside between the light source system 104 and at least a portion of the ultrasonic receiver system 102, on at least a portion of the ultrasonic receiver system 102, or combinations thereof. In some examples, the noise reduction system 110 may include one or more electromagnetically shielded transmission wires. In some such examples, the one or more electromagnetically shielded transmission wires may be configured to reduce electromagnetic interference from circuitry of the light source system 104, receiver system circuitry, or combinations thereof, that is received by the ultrasonic receiver system 102. In some examples, the one or more electromagnetically shielded transmission wires, sound-absorbing layers, acoustic isolation material, light-absorbing material, light-reflecting material, or combinations thereof may be components of the ultrasonic receiver system 102, the light source system 104, or both. Despite the fact that the ultrasonic receiver system 102, the light source system 104 and the noise reduction system 110 are shown in FIG. 1 as being separate elements, such components may nonetheless be regarded as elements of the noise reduction system 110.

The apparatus 100 may be used in a variety of different contexts, many examples of which are disclosed herein. For example, in some implementations a mobile device may include the apparatus 100. In some such examples, the mobile device may be a smart phone. In some implementations, a wearable device may include the apparatus 100. The wearable device may, for example, be a bracelet, an armband, a wristband, a watch, a ring, a headband or a patch. Accordingly, in some examples the apparatus 100 may be configured to be worn by, or attached to, a person.

Figure 2A:
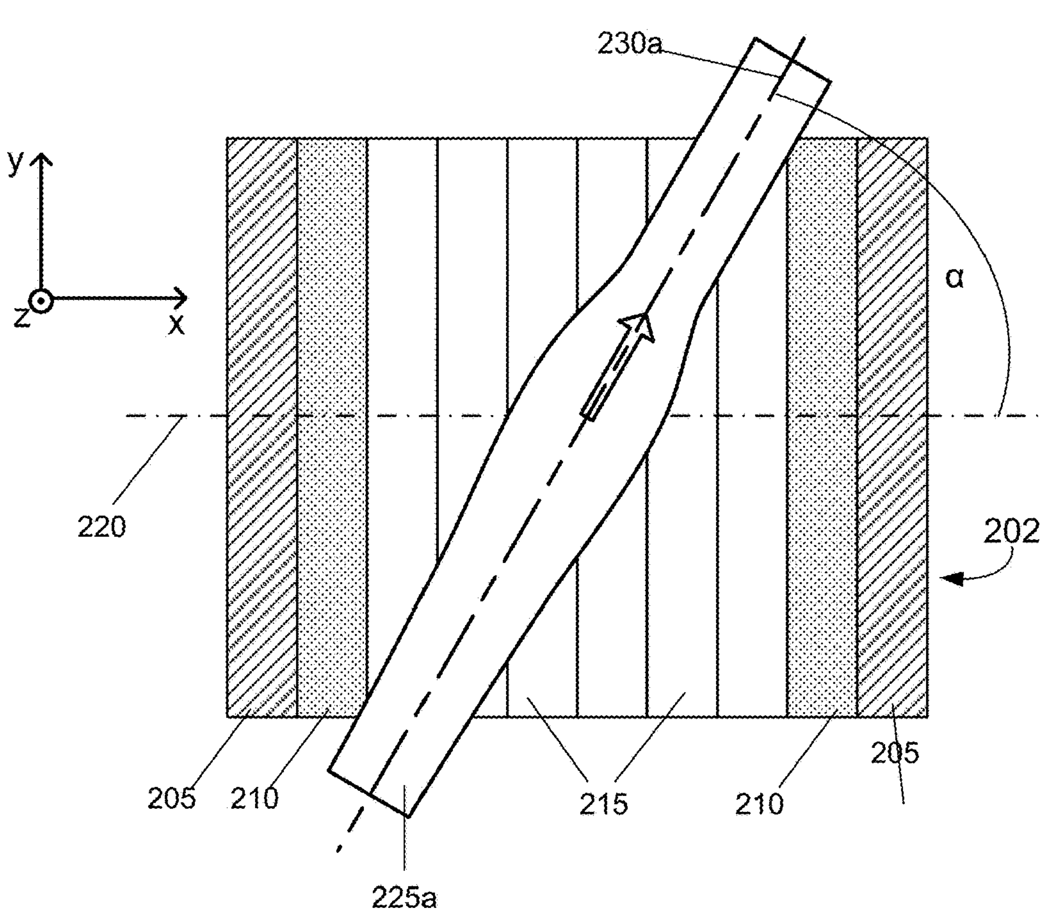
FIGS. 2A and 2B show examples of ultrasonic receiver element arrays.
Figure 2B:
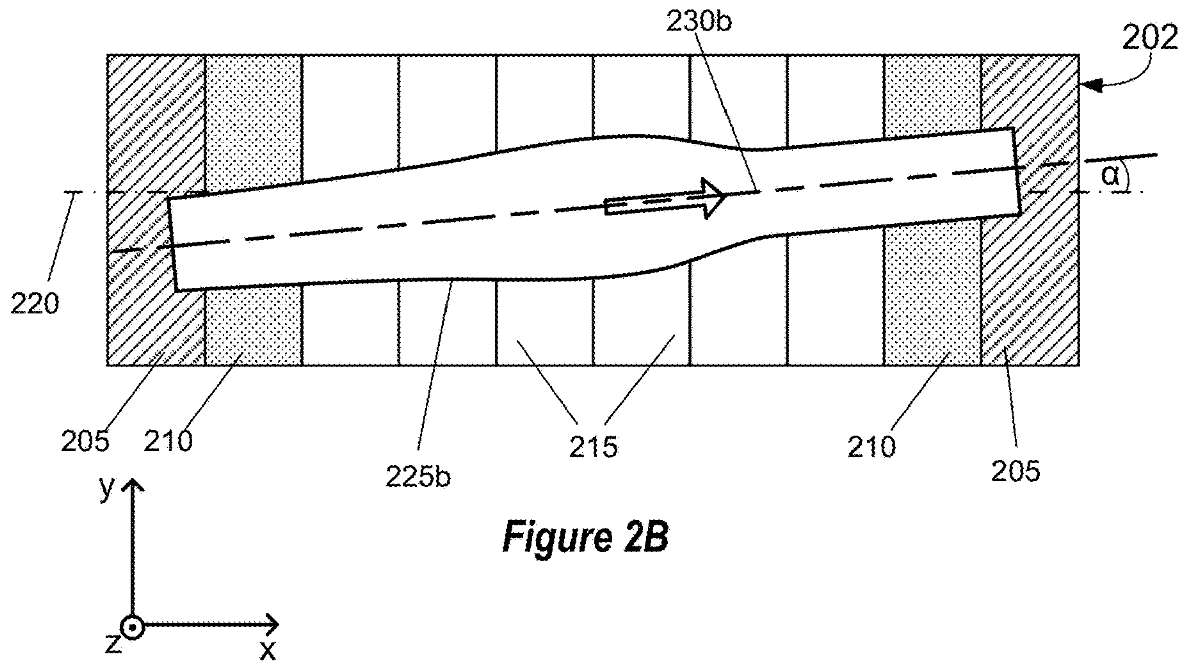

FIGS. 2A and 2B show examples of ultrasonic receiver element arrays. In these examples, the array axes 220 correspond with an x axis of a coordinate system. According to these examples, the arrays of ultrasonic receiver elements 202 each include two ground elements 205, two inactive or "dead" ultrasonic receiver elements 210 and six active ultrasonic receiver elements 215. The arrows shown within the blood vessels 225*a* and 225*b* indicate directions of blood flow. As with other disclosed examples, the types, numbers, sizes and arrangements of elements shown in FIGS. 2A and 2B and described herein are merely examples.

According to the examples shown in FIGS. 2A and 2B, each of the active ultrasonic receiver elements 215 extends farther in the y direction than in the x direction. In other words, in these examples each of the active ultrasonic receiver elements 215 extends farther in a direction that is perpendicular to the axis 220 than in a direction the axis 220. For the sake of convenience, the dimension of an active ultrasonic receiver element 215 in the x direction may be called the width and the dimension of an active ultrasonic receiver element 215 in the y direction may be called the length.

In some examples, the active ultrasonic receiver elements 215 of FIGS. 2A and 2B may have a length on the order of millimeters (mm), such as 2 mm, 3 mm, 4 mm, 5 mm, 6 mm, etc. According to some examples, the active ultrasonic receiver elements 215 of FIG. 2A may have a width that is less than the width of the active ultrasonic receiver elements 215 of FIG. 2B. In some such examples, the active ultrasonic receiver elements 215 of FIG. 2A may have a width of less than 1 mm, such as 0.4 mm, 0.45 mm, 0.5 mm, 0.55 mm, 0.6 mm, 0.65 mm, 0.7 mm, 0.75 mm, 0.8 mm, 0.85 mm, 0.9 mm, etc. According to some examples, the active ultrasonic receiver elements 215 of FIG. 2B may have a width greater than 1 mm, such as 1.1 mm, 1.15 mm, 1.2 mm, 1.25 mm, 1.3 mm, 1.35 mm, 1.4 mm, 1.45 mm, 1.5 mm, etc. In some examples, a kerf or separation between adjacent active ultrasonic receiver elements 215 may be less than 0.1 mm, such as 0.030 mm, 0.040 mm, 0.050 mm, 0.060 mm, 0.070 mm, etc.

According to some examples, the pitch between adjacent active ultrasonic receiver elements 215 may be equal to a wavelength corresponding to the peak frequency of ultrasonic waves generated by the target object responsive to the light from the light source system. In some examples, the peak frequency may be in the range from 1 MHz to 12 MHz.

However, in some alternative examples, the pitch between adjacent active ultrasonic receiver elements 215 may be a multiple of a half wavelength corresponding to the peak frequency of ultrasonic waves generated by the target object responsive to the light from the light source system. In some such examples, the array of ultrasonic receiver elements 202 may be a phased array of ultrasonic receiver elements. The multiple may be 1, 2, 3, 4, etc.

According to some examples, the array of ultrasonic receiver elements 202 may be an array of electrodes arranged on a piezoelectric layer. The piezoelectric layer may be, or may include, lead zirconate titanate (PZT), a piezoelectric composite, or a combination thereof. The composite piezoelectric material may, for example, be a 1-3 composite, a 2-2 composite, a 3-3 composite, etc.

In the example shown in FIG. 2A, the array of ultrasonic receiver elements 202 is arranged along an array axis 220 that is configured to extend across the blood vessel 225*a*. In this example, the portion of the blood vessel 225*a* that is shown in FIG. 2A extends along a blood vessel axis 230*a*. According to this example, the angle α between the array axis 220 and the blood vessel axis 230*a* is greater than 45 degrees. In some examples, the angle α may be greater than 60 degrees, greater than 75 degrees, etc. Having the angle α be close to 90 degrees, such as in a range from 70 degrees to 110 degrees, can be advantageous for imaging a cross-section of a blood vessel. Such images may be useful for detecting changes in blood vessel diameter during the systolic and diastolic phases of the cardiac cycle.

In the example shown in FIG. 2B, the array of ultrasonic receiver elements 202 is arranged along an array axis 220 that is configured to extend along the blood vessel 225*b*. In this example, the portion of the blood vessel 225*b* that is shown in FIG. 2B extends along a blood vessel axis 230*b*. According to this example, the angle α between the array axis 220 and the blood vessel axis 230*b* is less than plus or minus 45 degrees. In other words, the absolute value of the angle α may be less than 45 degrees. In some examples, the absolute value of the angle α may be less than 30 degrees, less than 20 degrees, etc. Having the absolute value of the angle α be close to zero degrees, such as in a range from −20 degrees to 20 degrees, can be advantageous for imaging along an axis of a blood vessel. Such images may be useful for detecting blood flow within the blood vessel, determining a local pulse wave velocity, etc.

Figure 3A:
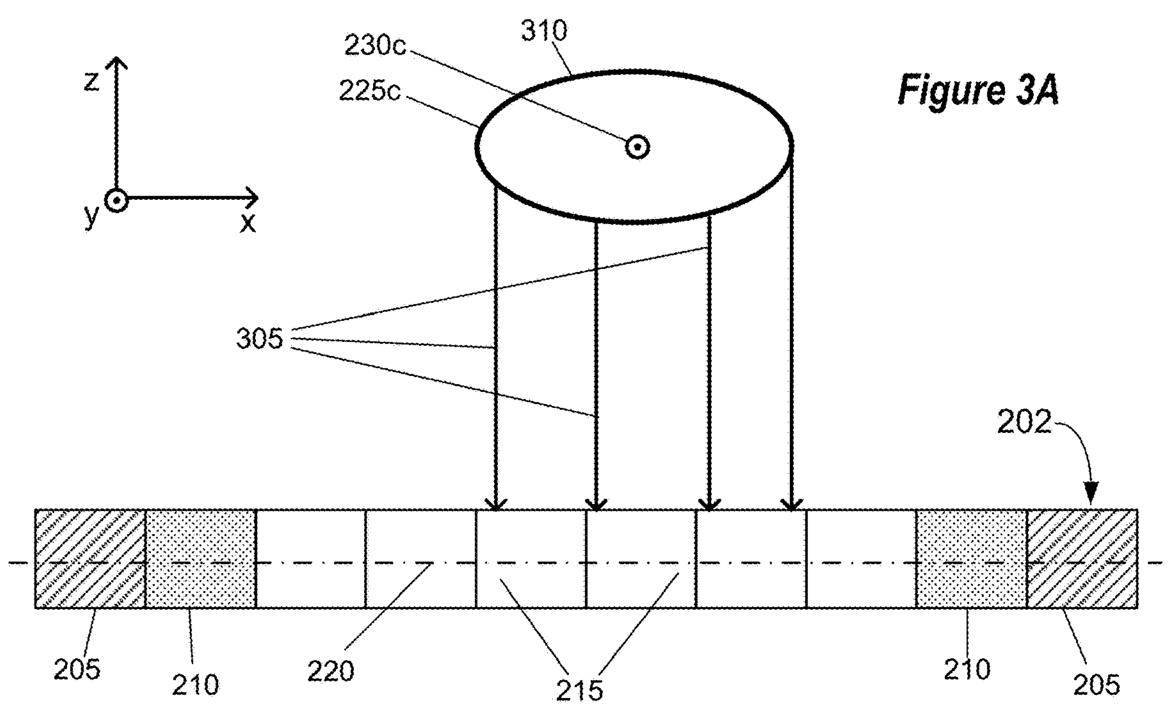
FIGS. 3A and 4A show additional examples of ultrasonic receiver element arrays.
Figure 3B:
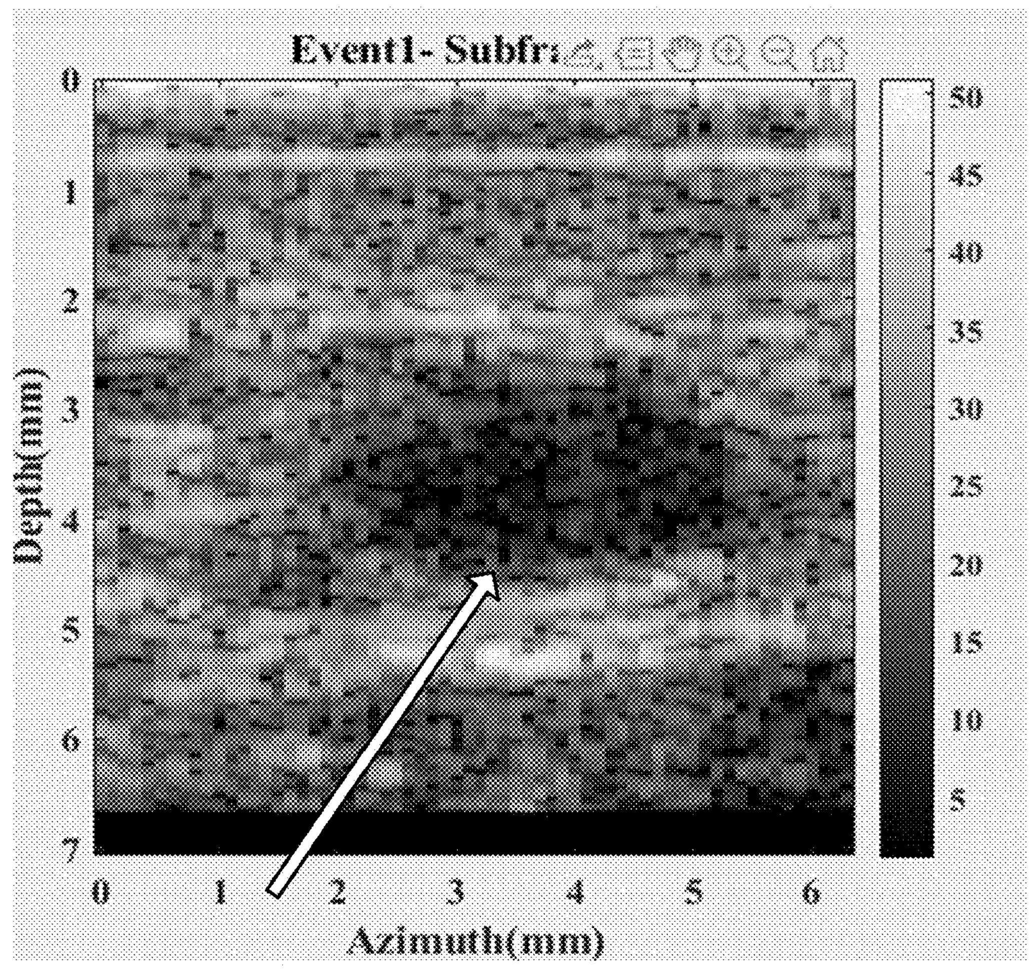
FIGS. 3B and 4B show examples of image data that may be obtained from the ultrasonic receiver element arrays shown in FIGS. 3A and 4A.
Figure 4A:
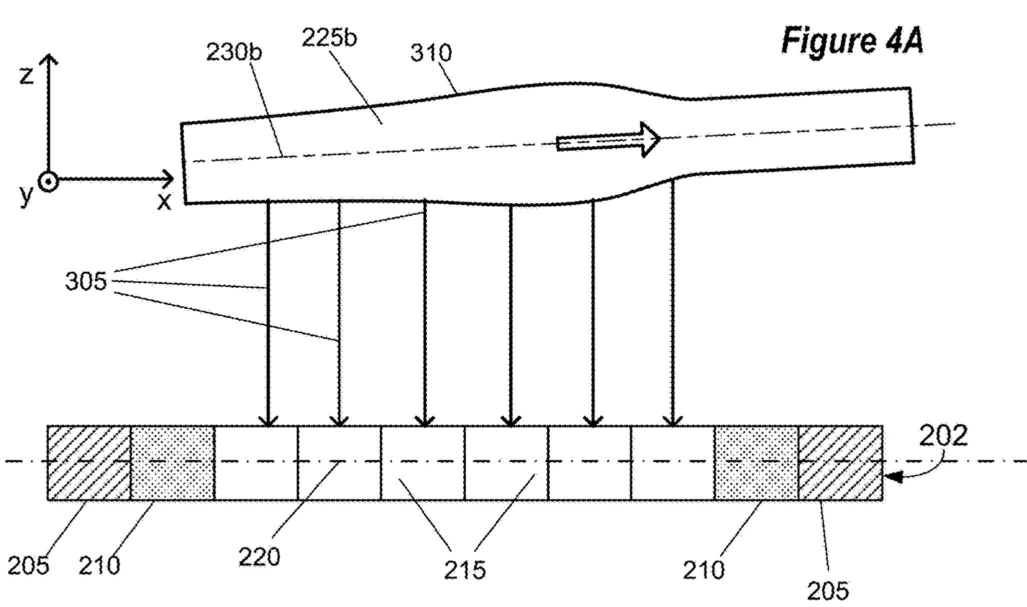
Figure 4B:
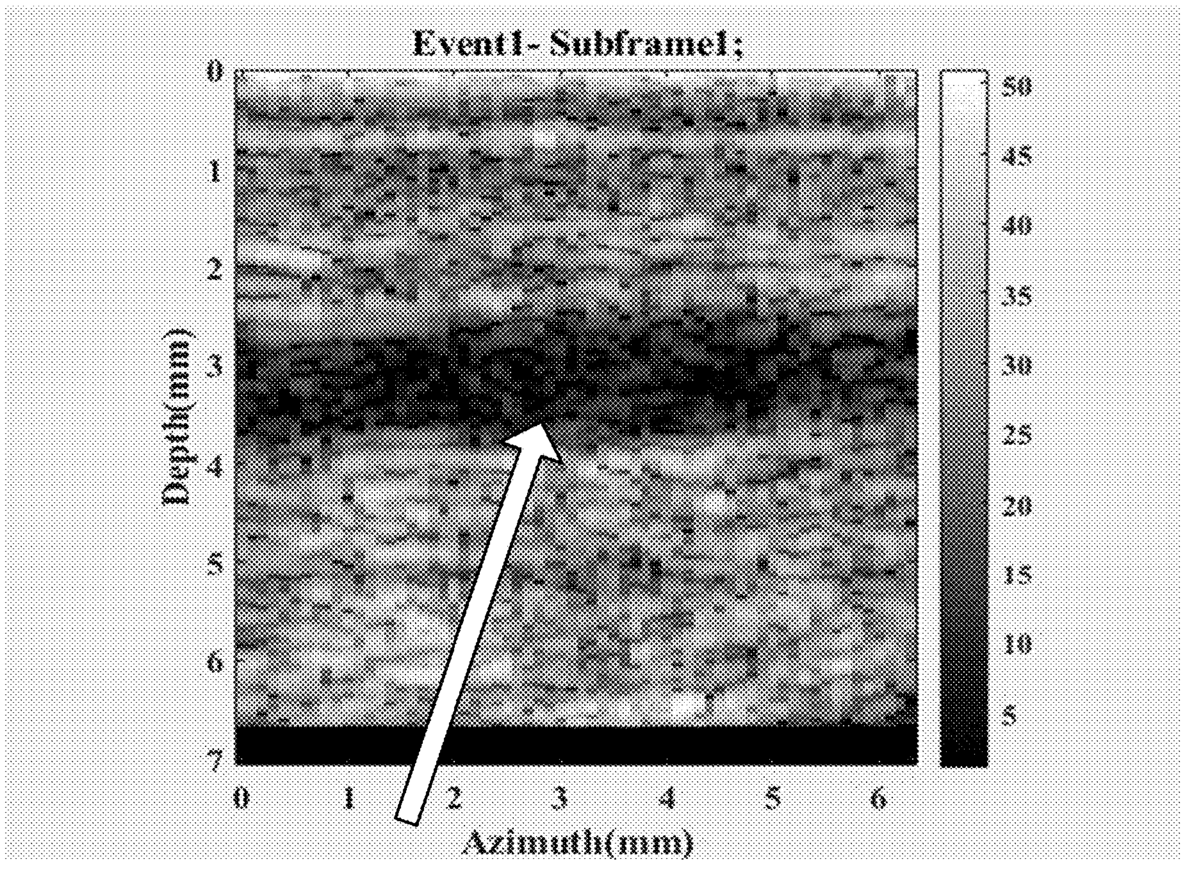

FIGS. 3A and 4A show additional examples of ultrasonic receiver element arrays. FIGS. 3B and 4B show examples of image data that may be obtained from the ultrasonic receiver element arrays shown in FIGS. 3A and 4A. In the examples shown in FIGS. 3A and 4A, the array axes 220 correspond with an x axis of a coordinate system, the viewing angle is along the y axis and blood vessels are shown separated from the arrays of ultrasonic receiver elements 202 in the z direction. As with other disclosed examples, the types, numbers, sizes and arrangements of elements shown in FIGS. 3A and 4A and described herein are merely examples.

The array of ultrasonic receiver elements 202 shown in FIG. 3A is arranged along an array axis 220 that is configured to extend across the blood vessel 225*c*. The array of ultrasonic receiver elements 202 shown in FIG. 3A may, in some examples, be similar to, or an instance of, the array of ultrasonic receiver elements 202 that is shown in FIG. 2A. However, in this example the blood vessel axis 230*c* is perpendicular to the array axis 220. According to this example, the arrows 305 shown in FIG. 3A correspond to ultrasonic waves caused by a photoacoustic response of a wall of the blood vessel 225*c* to light provided by a light source system 104 (not shown in FIG. 3A).

The image data shown in FIG. 3B corresponds to ultrasonic waves received at an instant in time by the array of ultrasonic receiver elements 202 of FIG. 3A from the blood vessel 225*c*. In this example, the tip of the arrow shown in FIG. 3B is touching an area of the image data corresponding to a blood vessel wall on a distal side 310 of the blood vessel 225*c* shown in FIG. 3A. Image data such as that shown in FIG. 3B, obtained over time, may be useful for detecting changes in blood vessel diameter during the systolic and diastolic phases of the cardiac cycle.

The array of ultrasonic receiver elements 202 shown in FIG. 4A is arranged along an array axis 220 that is configured to extend across the blood vessel 225*b*. The array of ultrasonic receiver elements 202 and the blood vessel 225*b* that are shown in FIG. 4A are instances of the array of ultrasonic receiver elements 202 and the blood vessel 225*b* that are shown in FIG. 2B. According to this example, the arrows 305 shown in FIG. 4A correspond to ultrasonic waves caused by a photoacoustic response of a wall of the blood vessel 225*b* to light provided by a light source system 104 (not shown in FIG. 4A).

The image data shown in FIG. 4B corresponds to ultrasonic waves received at an instant in time by the array of ultrasonic receiver elements 202 of FIG. 4A from the blood vessel 225*b*. In this example, the tip of the arrow shown in FIG. 4B is touching an area of the image data corresponding to a blood vessel wall on a distal side 310 of the blood vessel 225*b* shown in FIG. 4A. Image data such as that shown in FIG. 4B, obtained over time, may be useful for detecting blood flow within the blood vessel 225*b*, determining a local pulse wave velocity, etc.

Figure 4C:
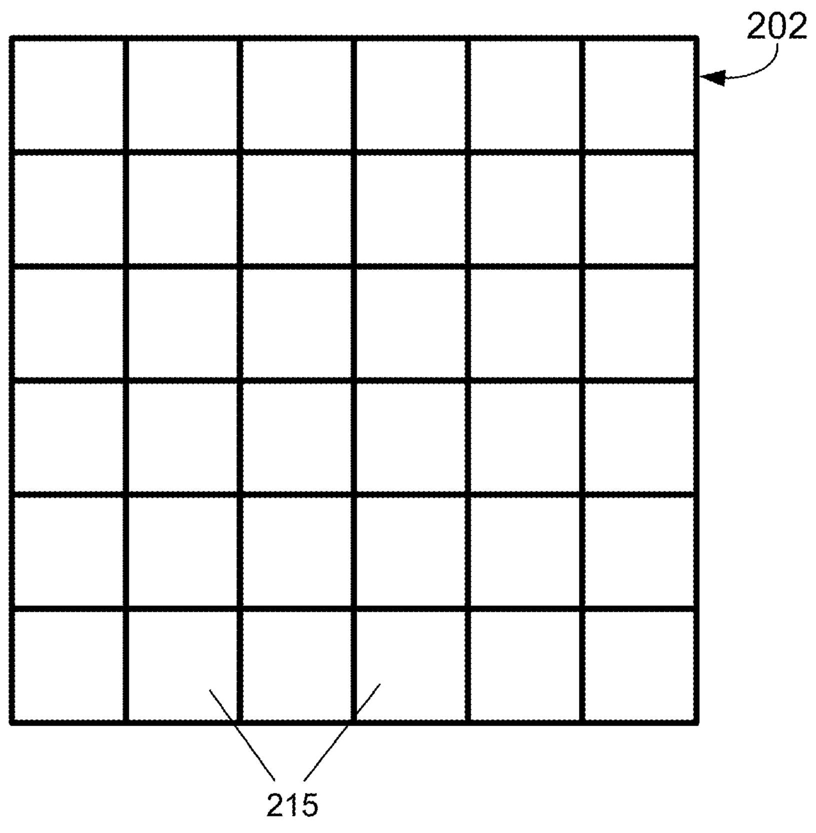
FIG. 4C shows another example of an ultrasonic receiver element array.

FIG. 4C shows another example of an ultrasonic receiver element array. In this example, the array of ultrasonic receiver elements 202 is a two-dimensional array of ultrasonic receiver elements. According to this example, the array of ultrasonic receiver elements 202 is arranged in a square having 6 active ultrasonic receiver elements 215 on each side and a total of 36 active ultrasonic receiver elements 215. As with other disclosed examples, the type, number, size and arrangement of elements shown in FIG. 4C and described herein are merely examples. For example, alternative examples of two-dimensional arrays of ultrasonic receiver elements may be arranged in a different shape, such as a non-square rectangular shape, a hexagonal shape, etc. Some alternative examples of two-dimensional arrays of ultrasonic receiver elements may include a different number of active ultrasonic receiver elements 215, such as 16, 20, 25, 30, 32, 36, 40, 48, etc.

Figure 5A:
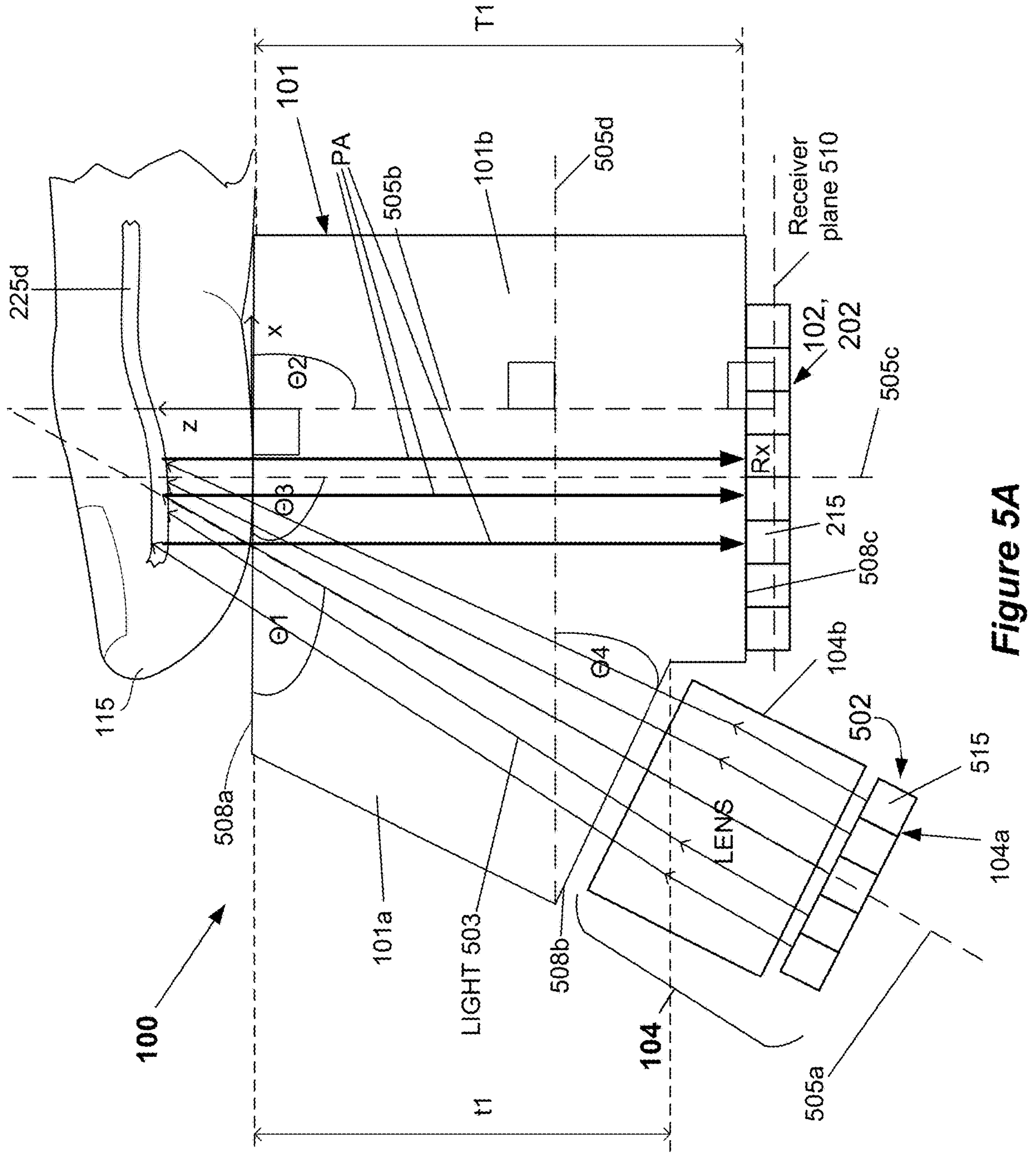
FIG. 5A shows example components of an apparatus according to some disclosed implementations.

FIG. 5A shows example components of an apparatus according to some disclosed implementations. As with other figures provided herein, the numbers, types and arrangements of elements shown in FIG. 5A are merely presented by way of example. In this example, the apparatus 100 is an instance of the apparatus 100 shown in FIG. 3. According to this example, the apparatus 100 includes a platen 101, a receiver system 102 and a light source system 104. In this example, an outer surface 508*a* of the platen 101 is configured to receive a target object, such as the finger 115, a wrist, etc. In this example, the finger 115 includes a blood vessel 225*d*.

According to this example, the light source system 104 includes a light-emitting portion 104*a* and a lens 104*b*. In this example, light-emitting portion 104*a* includes an array of light-emitting elements 502. According to this example, the array of light-emitting elements 502 includes at least five individual light-emitting elements 515. In some examples, the array of light-emitting elements 502 may be a two-dimensional array of individual light-emitting elements 515. The light-emitting elements 515 may, for example, include light-emitting diodes, laser diodes, VCSELs, edge-emitting lasers, neodymium-doped yttrium aluminum garnet (Nd:YAG) lasers, or combinations thereof. Light source systems 104 that include an array of light-emitting elements 502 can be particularly beneficial for implementations that also include an array of ultrasonic receiver elements 202. An array of light-emitting elements 502 can illuminate a larger portion of a target object than a single light-emitting element. Moreover, an array of light-emitting elements 502—as compared to a single light-emitting element-provides a greater variety of trajectories along which light travels within a target object and a greater variety of trajectories along which ultrasound produced by the photoacoustic effect may travel within the target object. In this example, the lens 104*b* is configured to focus the light 503 emitted by the light-emitting portion 104*a* into a relatively smaller cross-sectional area, which increases the intensity of the light 503 received by a target object (such as the finger 115) on the outer surface 508*a*. Although FIG. 5A shows the light-emitting portion 104*a* and the lens 104*b* separated by a gap, the light-emitting portion 104*a* and the lens 104*b* will generally be positioned adjacent to one another.

In this example, the platen 101 includes platen portion 101*a* and platen portion 101*b*. According to this example, the platen portion 101*a* has a thickness of t1, which is less than the thickness T1 of the platen portion 101*b*. In this example, the platen portion 101*a* includes a surface 508*b* that is configured to receive the light 503 from the light source system 104. Although FIG. 5A shows the light source system 104 separated from the surface 508*b* by a gap, in some examples the light source system 104 will be positioned adjacent to the surface 508*b*, without a gap. According to this example, the platen portion 101*a* is configured to direct the light 503 from the light source system 104 towards the outer surface 508*a* and towards a target object, if any, on the outer surface 508*a*.

According to this example, the platen 101 (more specifically, the platen portion 101*a*) and the light source system 104 are configured for transmitting light 503 from the light source system 104 to the outer surface 508*a* of the platen 101 along a first axis, or substantially along a first axis, which is oriented at a first angle relative to the outer surface 508*a*. In FIG. 5A, the axis 505*a* is an example of the first axis and the angle Θ1 is an example of the first angle. In this context, "substantially along the first axis" or "substantially parallel to the first axis" may mean within an angle range of plus or minus 10 degrees of the first axis, within an angle range of plus or minus 15 degrees of the first axis, within an angle range of plus or minus 20 degrees of the first axis, within an angle range of plus or minus 25 degrees of the first axis, within an angle range of plus or minus 30 degrees of the first axis, or within another such angle range. According to this example, the axis 505*a* is perpendicular to the surface 508*b*.

In this example, the receiver system 102, which is an ultrasonic receiver system in this implementation, resides adjacent to a surface 508*c* of the platen 101 (more specifically, of the platen portion 101*b*). According to this example, the receiver system 102 includes an array of ultrasonic receiver elements 202 that resides in a receiver plane 510 that is oriented parallel to the surface 508*c*. In this example, the array of ultrasonic receiver elements 202 includes at least a linear array of active ultrasonic receiver elements 215. In some examples, the array of ultrasonic receiver elements 202 may include a two-dimensional array of active ultrasonic receiver elements 215. In this example, a normal to the receiver plane 510 is oriented along a second axis, which in this example is the axis 505*b*, that is oriented at a second angle relative to the outer surface 508*a*. In FIG. 5A, the angle Q2 is an example of the second angle. In this example, the receiver plane 510 is parallel to the outer surface 508*a*, so the angle Θ2 is 90 degrees.

According to this example, the platen 101 (more specifically, the platen portion 101*b*) is configured to direct acoustic waves, including photoacoustic waves PA, emitted by a target object on the outer surface 508*a* towards the receiver system 102. In this example, the platen 101 (more specifically, the platen portion 101*b*) is configured for transmitting acoustic waves, including but not limited to ultrasonic waves, generated by a target object on the outer surface 508*a* towards the receiver system 102 along a third axis, or substantially along the third axis, which is oriented at a third angle relative to the outer surface 508*a*. In FIG. 5A, the axis 505*c* is an example of the third axis and the angle Θ3 is an example of the third angle. In this context, "substantially along the third axis" or "substantially parallel to the third axis" may mean within an angle range of plus or minus 10 degrees of the third axis, within an angle range of plus or minus 15 degrees of the third axis, within an angle range of plus or minus 20 degrees of the third axis, within an angle range of plus or minus 25 degrees of the third axis, within an angle range of plus or minus 30 degrees of the third axis, or within another such angle range. According to this example, the platen portion 101*b* is shown to be transmitting arterial photoacoustic waves PA substantially along the axis 505*c*. In this example, the second axis is parallel to, or substantially parallel to the third axis (for example, within +/−5 degrees of being parallel, within +/−10 degrees of being parallel, within +/−15 degrees of being parallel, within +/−20 degrees of being parallel, etc.).

In this example, the third axis is not parallel to the first axis, but instead is separated from the first axis by an angle (Θ3−Θ1). In some examples, the angle (Θ3−Θ1) may be in the range of 20 degrees to 60 degrees. According to some alternative examples, the third axis may be parallel to the first axis. However, in some alternative examples, the first axis may be parallel to, or substantially parallel to (for example, within +/−5 degrees of being parallel, within +/−10 degrees of being parallel, within +/−15 degrees of being parallel, within +/−20 degrees of being parallel, etc.) the third axis.

The first, second and third axes may, in some examples, be defined by a coordinate system that is relative to the apparatus 100 or a portion thereof. In the example shown in FIG. 5A, a Cartesian coordinate system is shown to be defined relative to the outer surface 508*a* of the platen 101.

In this example, an axis 505*d* is parallel to the outer surface 508*a*. An angle Θ4 is shown between the axis 505*d* and the surface 508*b*, indicating that the angle between the surface 508*b* and the outer surface 508*a* is also Θ4. According to this example, Θ4=Θ3−Θ1.

In some implementations, the platen 101 (for example, at least part of the platen portion 101*b*) may include an acoustic waveguide. In some such implementations, the platen portion 101*b* may be configured for transmitting ultrasonic waves generated by a target object on the outer surface 508*a* towards the receiver system 102, via the acoustic waveguide.

According to some examples, the platen 101 may include one or more anti-reflective layers. In some examples, one or more anti-reflective layers may reside on the platen 101, or proximate the platen 101, for example on or proximate the outer surface 508*a*.

Figure 5B:
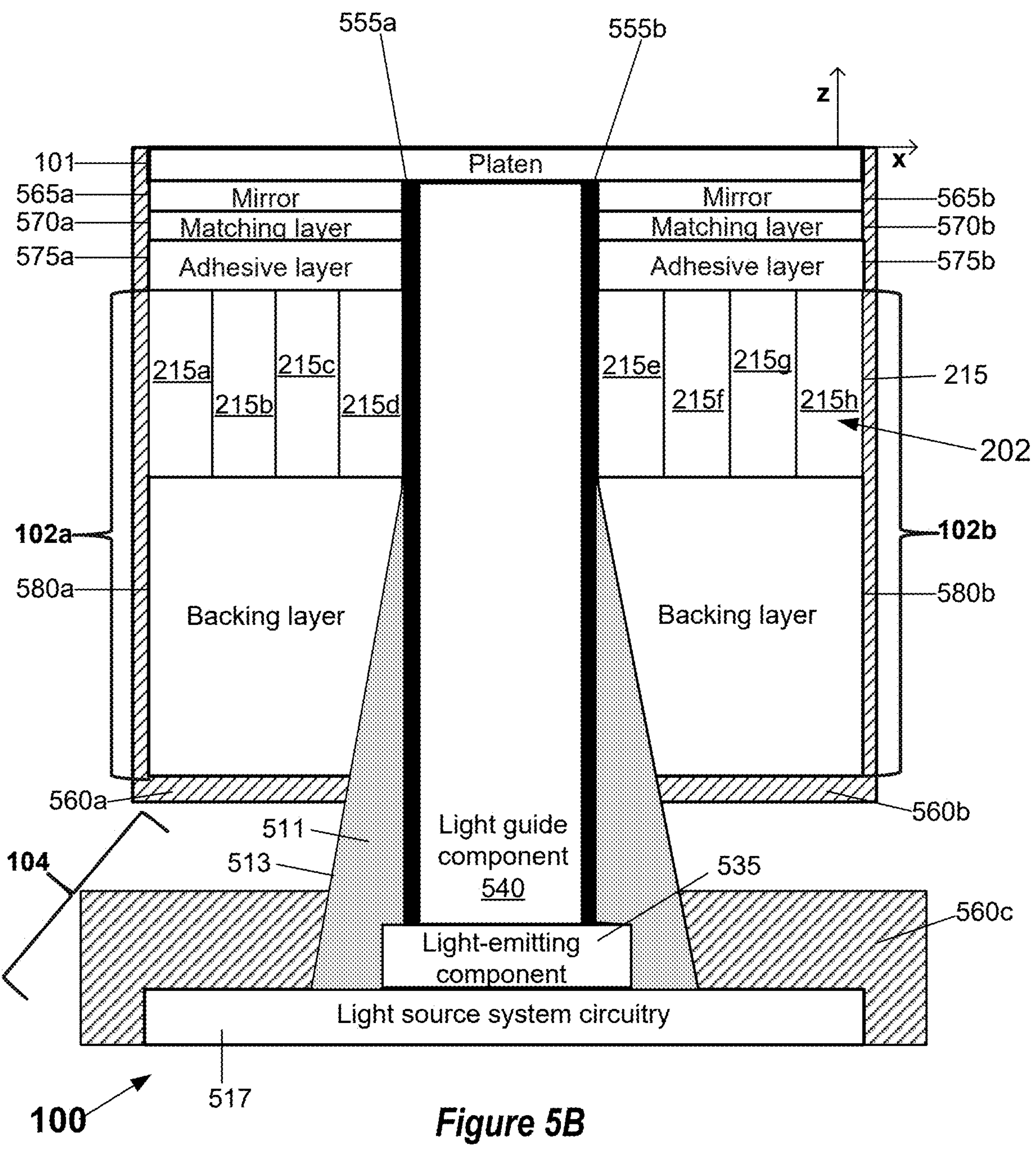
FIG. 5B shows example components of an apparatus according to some alternative implementations.

FIG. 5B shows example components of an apparatus according to some alternative implementations. As with other figures provided herein, the numbers, types and arrangements of elements shown in FIG. 5B are merely presented by way of example. In this example, the apparatus 100 is an instance of the apparatus 100 shown in FIG. 1.

In this example, the receiver stack portion 102*a* includes ultrasonic receiver elements 215*a*, 215*b*, 215*c* and 215*d*, as well as the backing layer 580*a*. Here, the receiver stack portion 102*b* includes ultrasonic receiver elements 215*e*, 215*f*, 215*g* and 215*h*, as well as the backing layer 580*b*. According to some implementations, the ultrasonic receiver elements 215*a*-215*d* may be elements of one linear or two-dimensional array, and the ultrasonic receiver elements 215*e*-215*h* may be elements of another linear or two-dimensional array. However, in some implementations, the ultrasonic receiver elements 215*a* and 215*h* may be part of the same ultrasonic receiver element ring. In some such implementations, the ultrasonic receiver elements 215*b* and 215*g* may be part of a second ultrasonic receiver element ring, the ultrasonic receiver elements 215*c* and 215*f* may be part of a third ultrasonic receiver element ring and the ultrasonic receiver elements 215*d* and 215*e* may be part of a fourth ultrasonic receiver element ring.

The backing layers 580*a* and 580*b* may be configured to suppress at least some acoustic artifacts and may provide a relatively higher signal-to-noise ratio (SNR) than receiver systems 102 that lack a backing layer. In some examples, the backing layers 580*a* and 580*b* may include metal, epoxy, or a combination thereof.

As described elsewhere herein, some implementations of the apparatus 100 include one or more elements configured for noise reduction. These noise reduction elements may be considered to be part of the noise reduction system 110 that is described with reference to FIG. 1. However, such noise reduction elements may reside in various parts of the apparatus 100.

One type of noise that may be present in the apparatus 100 involves the leakage of light from the light source system 104, such as from the light guide component 540 of FIG. 5B, to the receiver system 102. According to the example shown in FIG. 5B, the apparatus 100 includes the light-mitigating element 555*a*, which resides between the light guide component 540 and the receiver stack portion 102*a*, and the light-mitigating element 555*b*, which resides between the light guide component 540 and the receiver stack portion 102*b*. In this example, the light-mitigating elements 555*a* and 555*b* also reside between the light guide component 540 and the mirror layers 565*a* and 565*b*, the matching layers 570*a* and 570*b*, and the adhesive layers 575*a* and 575*b*. In some examples, the light-mitigating elements 555*a* and 555*b* may be discrete elements, whereas in other examples the light-mitigating elements 555*a* and 555*b* may be portions of a continuous element, such as a cylinder that surrounds the light guide component 540. In some examples, the light-mitigating elements 555*a* and 555*b* may include material having a relatively low index of refraction, such as a low refractive index foam. In this example, the light-mitigating elements 555*a* and 555*b* are configured to increase optical coupling and reduce optical losses.

Another type of noise that may be present in the apparatus 100 involves EMI from the light source system circuitry 517 that may be received by the receiver system 102. In the example shown in FIG. 5B, the apparatus 100 includes the EMI-reducing element 560*a* proximate the receiver stack portion 102*a* and the EMI-reducing element 560*b* proximate the receiver stack portion 102*b*. In some examples, the EMI-reducing elements 560*a* and 560*b* may include one or more types of EMI shielding material. According to some examples, the EMI-reducing elements 560*a* and 560*b* may be portions of a continuous element, such as a cylinder. In this example, the EMI-reducing element 560*c* resides between the light source system circuitry 517 and the receiver stack portions 102*a* and 102*b*. In some examples, the EMI-reducing element 560*c* may surround the light source system circuitry 517.

According to the example shown in FIG. 5B, the apparatus 100 includes a light-coupling component 511, which is configured to couple light from the light-emitting component 535 into the light guide component 540. In this example, the light-coupling component 511 has an outer surface 513 that is frustum-shaped. According to this example, the light-coupling component 511 resides partially between the receiver stack portions 102*a* and 102*b* and the light guide component 540, in order to reduce the overall thickness of the apparatus 100 along the z axis. Although some other disclosed implementations are not shown to have a light-coupling component, alternative examples of such disclosed implementations may, in fact, include one or more light-coupling components.

Figure 6:
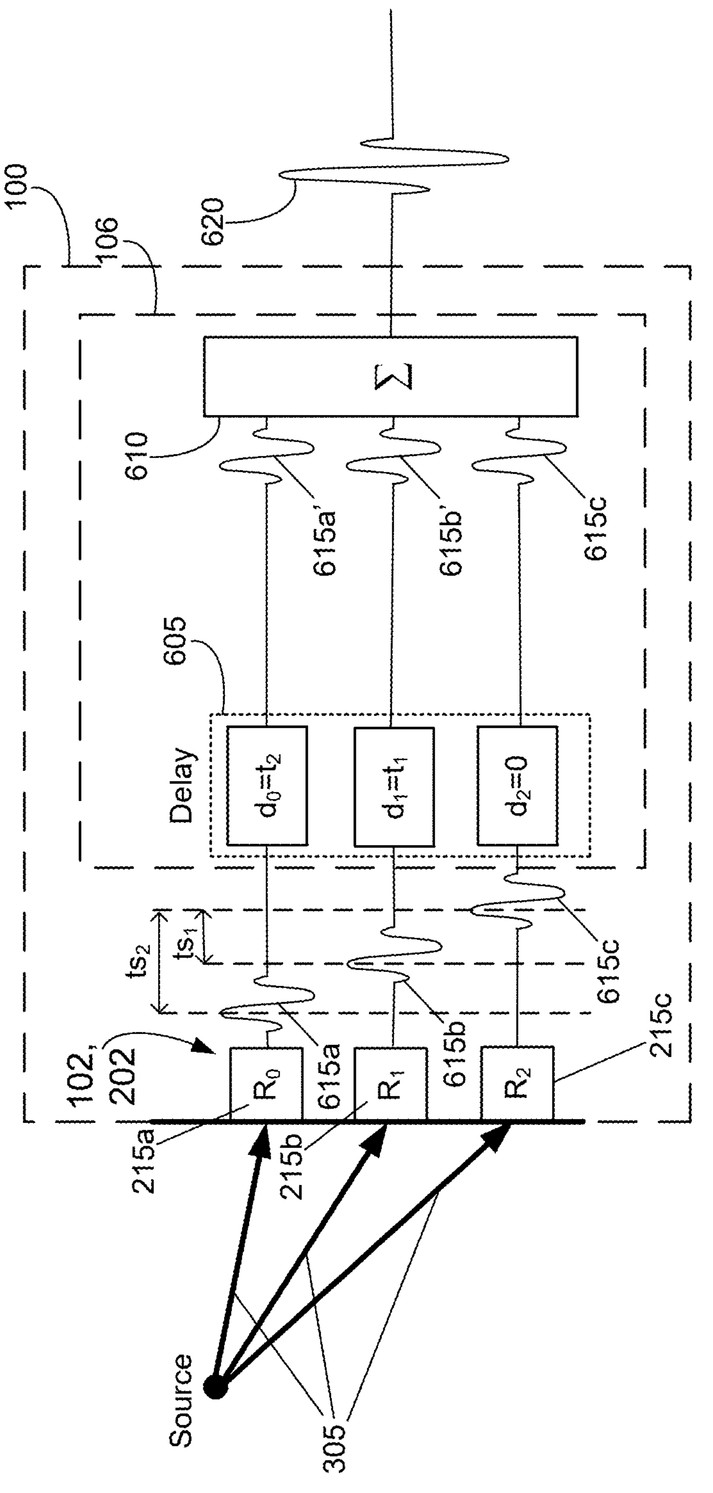
FIG. 6 shows an example of an apparatus that is configured to perform a receiver-side beamforming process.

FIG. 6 shows an example of an apparatus that is configured to perform a receiver-side beamforming process. In this example, the receiver-side beamforming process is a delay-and-sum beamforming process. As with other disclosed examples, the types, numbers, sizes and arrangements of elements shown in FIG. 6 and described herein, as well as the associated described methods, are merely examples.

In this example, a source is shown emitting ultrasonic waves 305, which are detected by active ultrasonic receiver elements 215*a*, 215*b* and 215*c* of an array of ultrasonic receiver elements 202. The array of ultrasonic receiver elements 202 is part of an ultrasonic receiver system 102. The ultrasonic waves 305 may, in some examples, correspond to the photoacoustic response of a target object to light emitted by a light source system 104 of the apparatus 100. In this example, the active ultrasonic receiver elements 215*a*, 215*b* and 215*c* provide ultrasonic receiver signals 615*a*, 615*b* and 615*c*, respectively, to the control system 106.

According to this example, the control system 106 includes a delay module 605 and a summation module 610. In this example, the delay module 605 is configured to determine whether a delay should be applied to each of the ultrasonic receiver signals 615*a*, 615*b* and 615*c*, and if so, what delay to apply. According to this example, the delay module 605 determines that a delay do of ts2 should be applied to the ultrasonic receiver signal 615*a*, that a delay d1 of ts1 should be applied to the ultrasonic receiver signal 615*b* and that no delay should be applied to the ultrasonic receiver signal 615*c* (because the delay d2=0). Accordingly, the delay module 605 applies a delay of t2 to the ultrasonic receiver signal 615*a*, producing the ultrasonic receiver signal 615*a*', and applies a delay of t1 to the ultrasonic receiver signal 615*b*, producing the ultrasonic receiver signal 615*b*'.

In some examples, the delay module 605 may determine what delay, if any, to apply to an ultrasonic receiver signal by performing a correlation operation on input ultrasonic receiver signals. For example, the delay module 605 may perform a correlation operation on the ultrasonic receiver signals 615*a* and 615*c*, and may determine that by applying a time shift of $t_2$ to the ultrasonic receiver signal 615*a*, the ultrasonic receiver signal 615*a* would be strongly correlated with the ultrasonic receiver signal 615*c*. Similarly, the delay module 605 may perform a correlation operation on the ultrasonic receiver signals 615*b* and 615*c*, and may determine that by applying a time shift of $t_1$ to the ultrasonic receiver signal 615*b*, the ultrasonic receiver signal 615*b* would be strongly correlated with the ultrasonic receiver signal 615*c*.

According to this example, the summation module 610 is configured to sum the ultrasonic receiver signals 615*a*', 615*b*' and 615*c*, producing the summed signal 620. One may observe that the amplitude of the summed signal 620 is greater than the amplitude of any one of the ultrasonic receiver signals 615*a*, 615*b* or 615*c*. In some instances, the signal-to-noise ratio (SNR) of the summed signal 620 may be greater than the SNR of any of the ultrasonic receiver signals 615*a*, 615*b* or 615*c*.

Figure 7A:
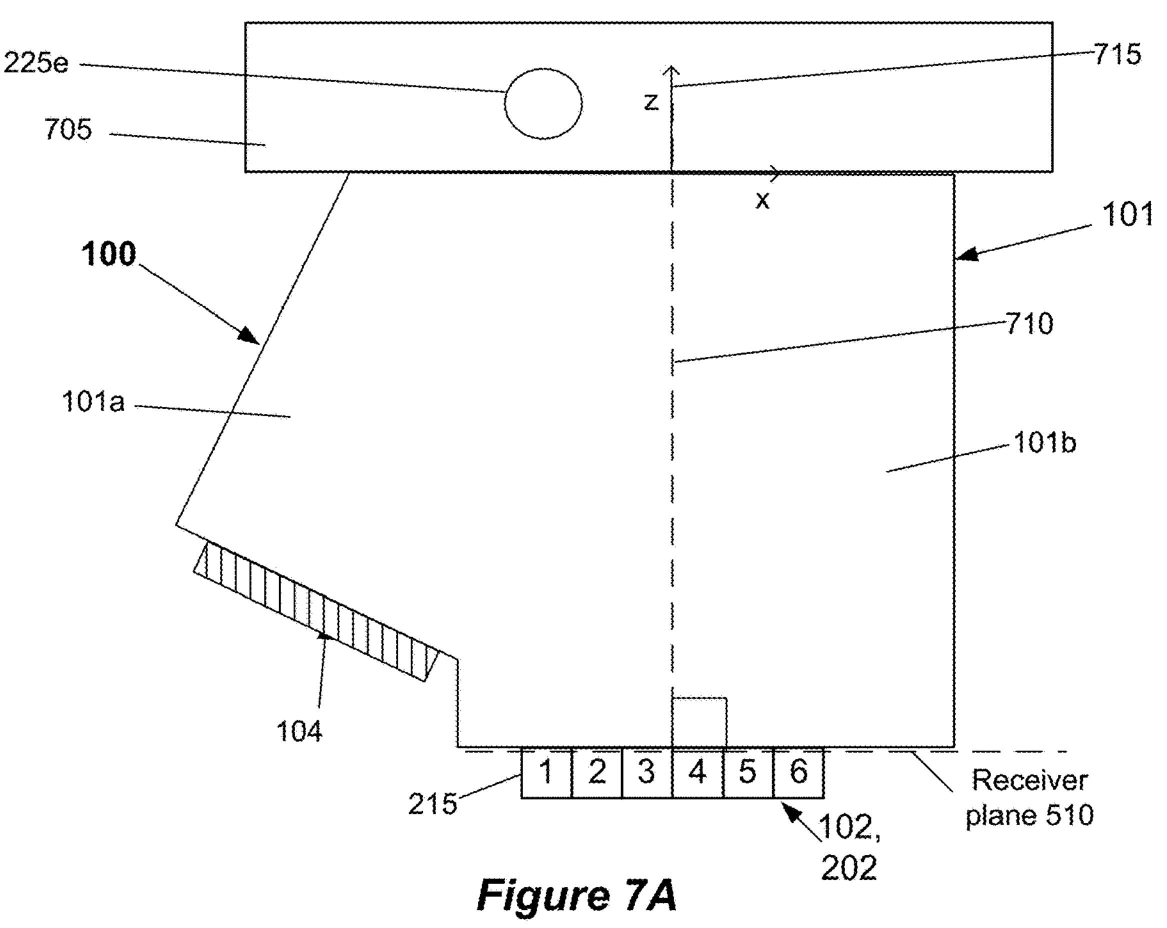
FIGS. 7A, 8A and 9A show examples of a photoacoustic plethysmography (PAPG)-capable apparatus and an artery in three different positions relative to the apparatus.
Figure 7B:
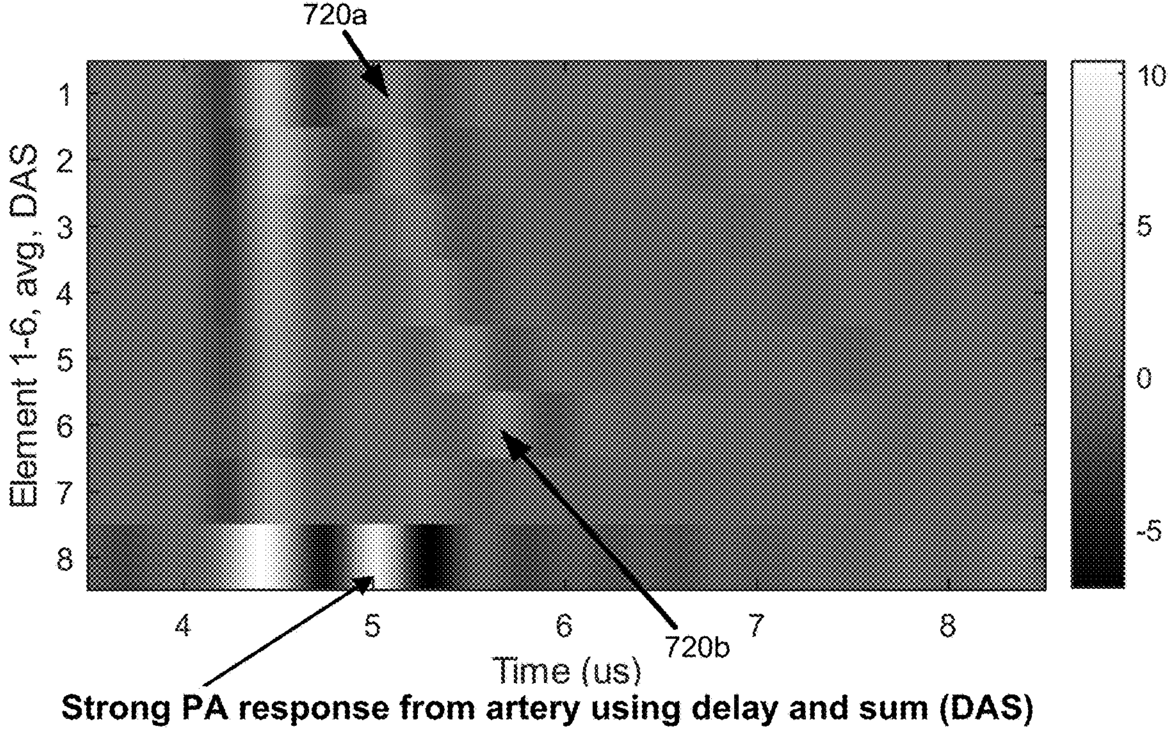
FIGS. 7B, 8B and 9B show examples of image data obtained by the PAPG-capable apparatus with the artery positions shown in FIGS. 7A, 8A and 9A, respectively.
Figures 8A, 8B:
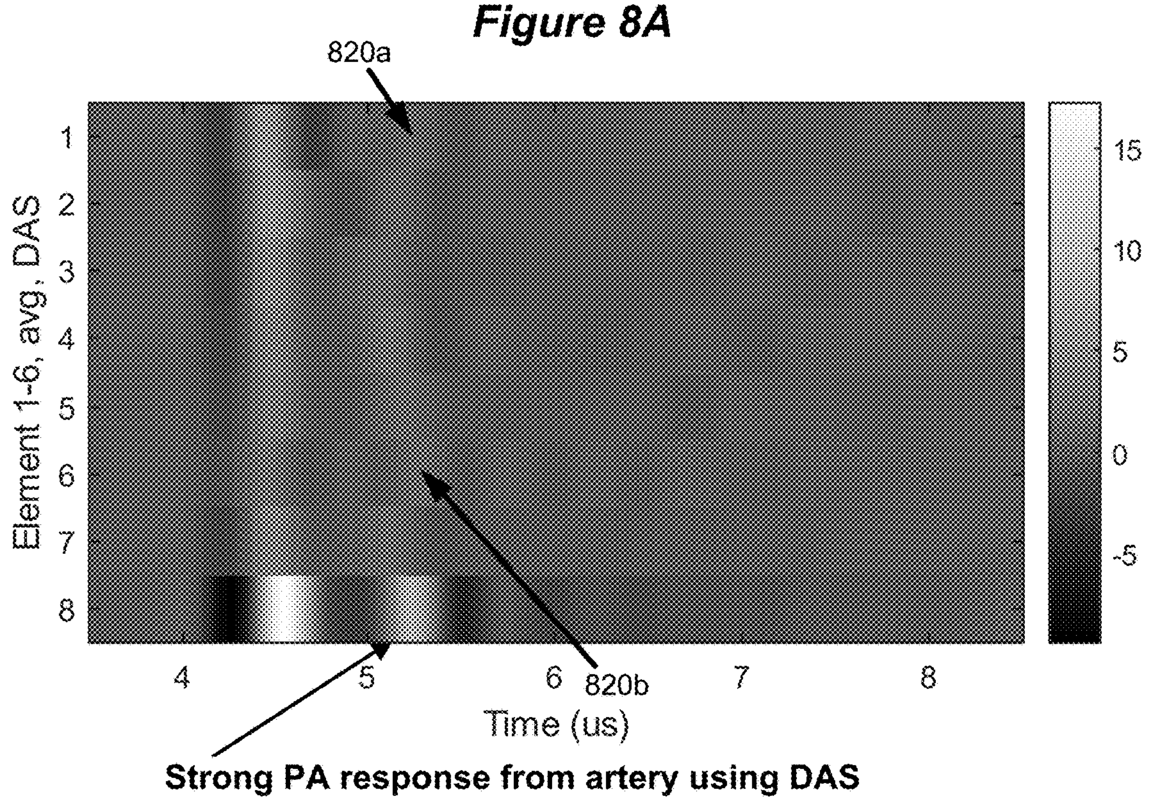
Figure 9A:
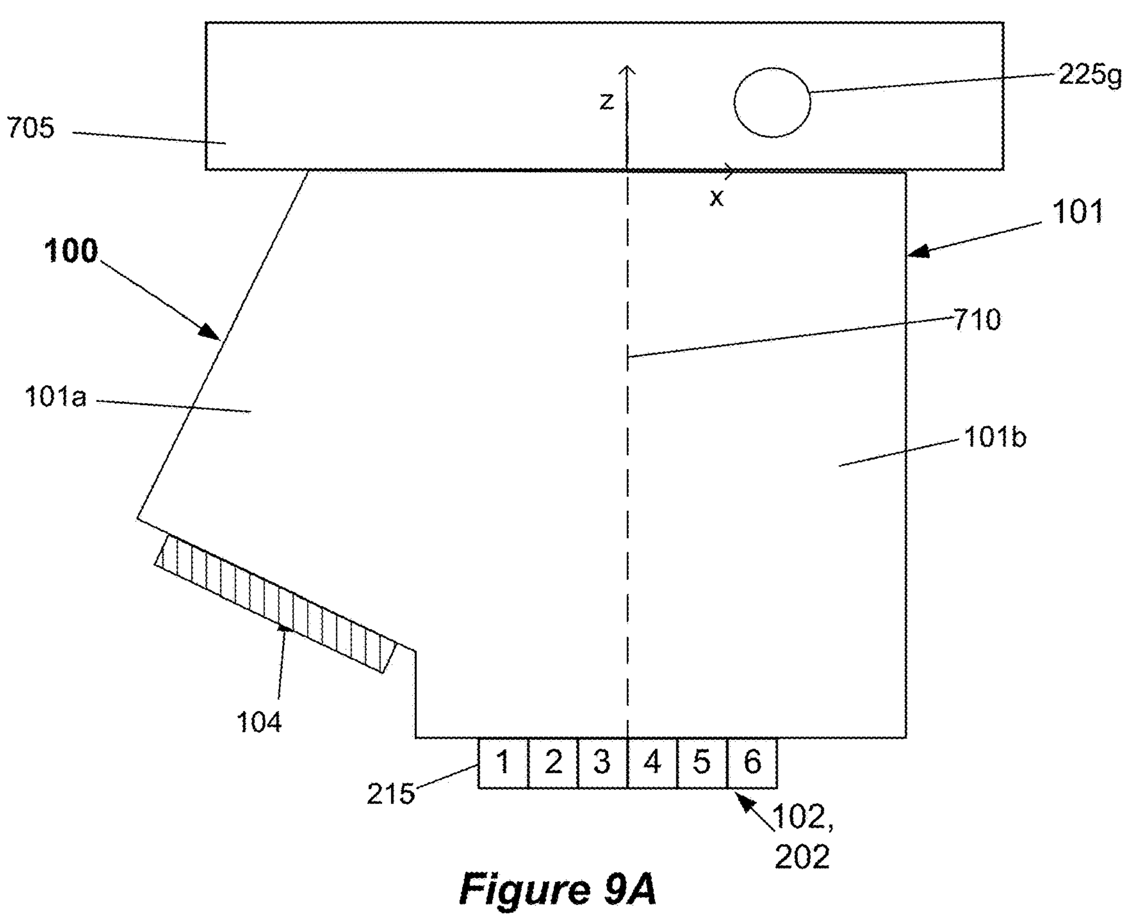
Figure 9B:
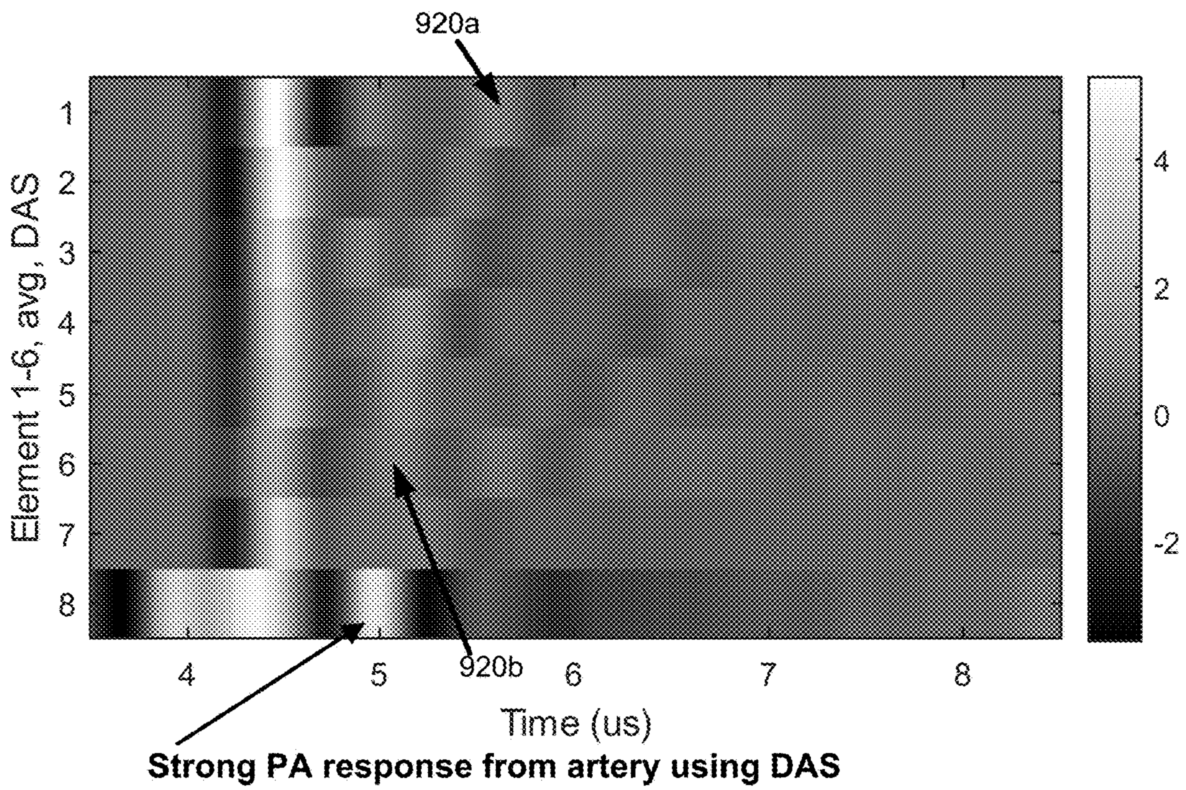

FIGS. 7A, 8A and 9A show examples of a photoacoustic plethysmography (PAPG)-capable apparatus and an artery in three different positions relative to the apparatus. FIGS. 7B, 8B and 9B show examples of image data obtained by the PAPG-capable apparatus with the artery positions shown in FIGS. 7A, 8A and 9A, respectively.

In the examples shown in FIGS. 7A, 8A and 9A, the apparatus 100 includes a platen 101, a light source system 104 and an ultrasonic receiver system 102 having an array of ultrasonic receiver elements 202. In these examples, the array of ultrasonic receiver elements 202 has 6 active ultrasonic receiver elements 215 residing in receiver plane 510. The active ultrasonic receiver elements 215 are numbered from 1 to 6 in these examples. According to these examples, a central axis 710 of the array of ultrasonic receiver elements 202 is perpendicular to the receiver plane 510. In these examples, the arteries 225*e*, 225*f* and 225*g* are all 2 mm in diameter and are located within a target object 705 in contact with the apparatus 100. The target object 705 is represented as a rectangle in FIGS. 7A, 8A and 9A for the sake of simplicity. As with other disclosed examples, the types, numbers, sizes and arrangements of elements shown in FIGS. 7A, 8A and 9A and described herein are merely examples.

FIGS. 7B, 8B and 9B show graphs of image data corresponding to signals from the array of ultrasonic receiver elements 202 shown in FIGS. 7A, 8A and 9A. In these examples, the numbers 1-6 along the vertical axes correspond to signals from the active ultrasonic receiver elements 215 that are numbered from 1-6 in FIGS. 7A, 8A and 9A. The number 7 on the vertical axes represents a summation of signals from the receiver elements 1-6. The number 8 on the vertical axes represents the output of a delay and sum (DAS) process, such as that disclosed herein with reference to FIG. 6.

In FIG. 7A, the artery 225*e* is located 3 mm from the central axis 710, in the negative x direction. In other words, the center of the artery 225*e* has an x coordinate of −3 mm relative to the coordinate system 715.

FIG. 7B shows image data that includes signals corresponding to the artery 225*e*. Reference number 720*a* indicates signals from receiver element 1 corresponding to the artery 225*e* and reference number 720*b* indicates signals from receiver element 6 corresponding to the artery 225*e*. Although one may readily observe these representations of arterial signals in FIG. 7B, as well as the representations of arterial signals from the receiver elements 2-5, the representations of the arterial signals shown in row 8 are much more pronounced after the DAS process, with a higher amplitude and a higher SNR. In contrast, merely taking an average of the signals from the receiver elements 1-6, as shown in row 7, decreases the amplitude of the representations of arterial signals.

One may also observe that the individual representations of arterial signals from the receiver elements 1-6 that are shown in rows 1-6 provide information about the position of the artery 225*e*. Because the arterial signals were received first by the receiver element 1 and were received last by the receiver element 6, it is apparent that the artery 225*e* is closest to the receiver element 1 and farthest from the receiver element 6.

In FIG. 8A, center of the artery 225*f* is located on the central axis 710. FIG. 8B shows image data that includes signals corresponding to the artery 225*f*. Reference number 820*a* indicates signals from receiver element 1 corresponding to the artery 225*f* and reference number 820*b* indicates signals from receiver element 6 corresponding to the artery 225*f*. Although one can see these representations of arterial signals in FIG. 8B, as well as the representations of arterial signals from the receiver elements 2-5, the representations of the arterial signals shown in row 8 have a higher amplitude and a higher SNR. Once again, merely taking an average of the signals from the receiver elements 1-6, as shown in row 7, decreases the amplitude of the representations of arterial signals.

The individual representations of arterial signals from the receiver elements 1-6 that are shown in rows 1-6 also provide information about the position of the artery 225*f*. Because the arterial signals were received first by the receiver elements 3 and 4, and were received last by the receiver elements 1 and 6, it is apparent that the artery 225*e* is on or near the central axis 710.

In FIG. 9A, the artery 225*g* is located 3 mm from the central axis 710, in the positive x direction. FIG. 9B shows image data that includes signals corresponding to the artery 225*g*. Reference number 920*a* indicates signals from receiver element 1 corresponding to the artery 225*g* and reference number 920*b* indicates signals from receiver element 6 corresponding to the artery 225*g*. As in the examples shown in FIGS. 7B and 8B, the representations of the arterial signals shown in row 8 are much more pronounced after the DAS process. However, merely taking an average of the signals from the receiver elements 1-6, as shown in row 7, decreases the amplitude of the representations of arterial signals.

Once again, the individual representations of arterial signals from the receiver elements 1-6 provide information about the position of the artery 225*g*. Because the arterial signals were received first by the receiver element 6 and were received last by the receiver element 1, it is apparent that the artery 225*g* is closest to the receiver element 6 and farthest from the receiver element 1.

Figure 10:
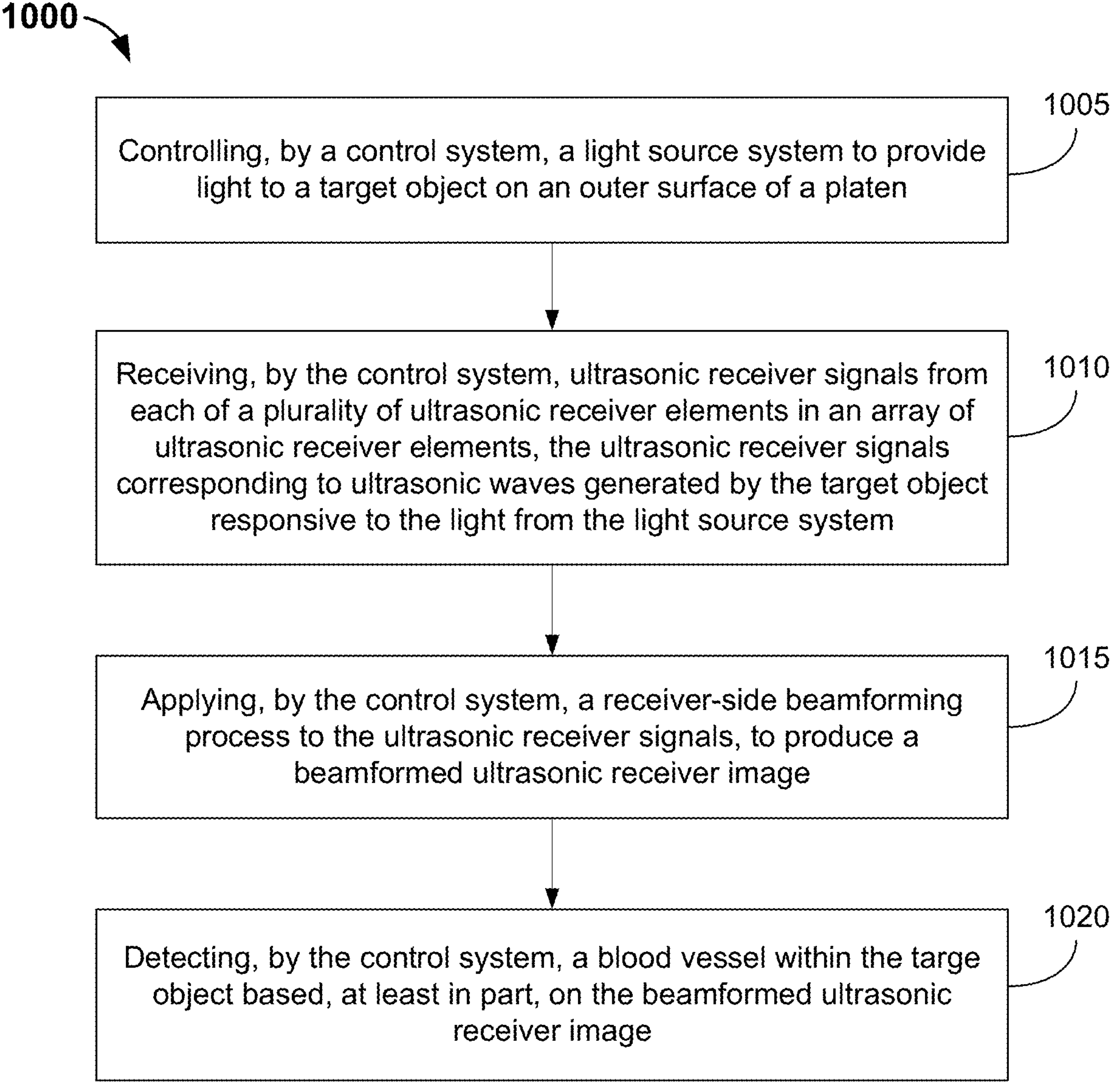
FIG. 10 is a flow diagram that shows examples of some disclosed operations.

FIG. 10 is a flow diagram that shows examples of some disclosed operations. The blocks of FIG. 10 may, for example, be performed by the apparatus 100 of FIG. 1 or by a similar apparatus. As with other methods disclosed herein, the method outlined in FIG. 10 may include more or fewer blocks than indicated. Moreover, the blocks of methods disclosed herein are not necessarily performed in the order indicated. In some instances, one or more of the blocks shown in FIG. 10 may be performed concurrently.

In this example, block 1005 involves controlling, by a control system, a light source system to provide light to a target object on an outer surface of a platen. The target object may be a finger, a wrist, etc., depending on the particular example. According to this example, block 1010 involves receiving, by the control system, ultrasonic receiver signals from each of a plurality of ultrasonic receiver elements in an array of ultrasonic receiver elements. In this example, the ultrasonic receiver signals correspond to ultrasonic waves generated by the target object responsive to the light from the light source system.

According to this example, block 1015 involves applying, by the control system, a receiver-side beamforming process to the ultrasonic receiver signals, to produce a beamformed ultrasonic receiver image. In some examples, the receiver-side beamforming process may be, or may include, a delay-and-sum beamforming process. Block 1015 may, for example, involve a process like that described with reference to FIG. 6. Other examples may involve other types of beamforming. In some such examples, beamforming may be based on algorithms developed according to machine learning techniques, for example machine learning techniques based on raw data corresponding to signals produced by individual ultrasonic receiver elements.

In this example, block 1020 involves detecting, by the control system, a blood vessel within the targe object based, at least in part, on the beamformed ultrasonic receiver image. In some examples, method 1000 may involve detecting the blood vessel within the target object based, at least in part, on the ultrasonic receiver signals.

The blood vessel may, for example, be detected according to a time window that corresponds with the speed of sound traversing an expected range of depth to a blood vessel. Alternatively, or additionally, the blood vessel may be detected according to one or more characteristics of the photoacoustic responses of the blood vessel walls, of blood within the blood vessel, or a combination thereof.

In some examples, method 1000 may involve estimating one or more blood vessel features based, at least in part, on the beamformed ultrasonic receiver image. The one or more blood vessel features may, for example, include blood vessel diameter, blood vessel area, blood vessel profile, blood vessel distention, volumetric flow, pulse wave velocity, blood vessel wall thickness, or combinations thereof. The one or more blood vessel features may, in some examples, be arterial features. In some examples, method 1000 may involve estimating one or more cardiac features based, at least in part, on the one or more blood vessel features. According to some such examples, method 1000 may involve estimating blood pressure based, at least in part, on the one or more blood vessel features. According to some examples, method 1000, may involve extracting and evaluating heart rate waveform (HRW) features.

Figure 11:
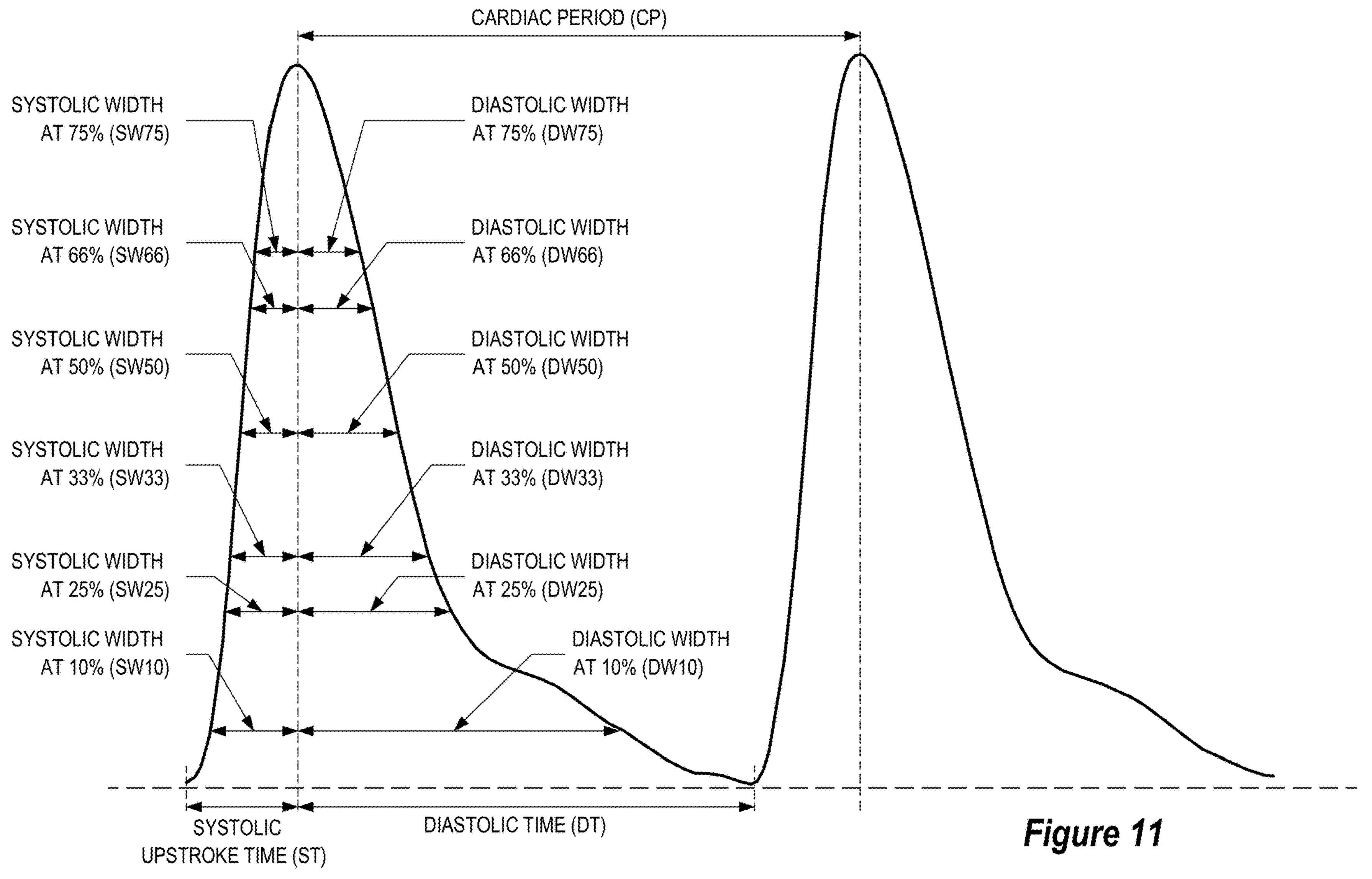
FIG. 11 shows examples of heart rate waveform (HRW) features that may be extracted according to some implementations of the method of FIG. 10.

FIG. 11 shows examples of heart rate waveform (HRW) features that may be extracted according to some implementations of the method of FIG. 10. The horizontal axis of FIG. 11 represents time and the vertical axis represents signal amplitude. The cardiac period is indicated by the time between adjacent peaks of the HRW. The systolic and diastolic time intervals are indicated below the horizontal axis. During the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

The HRW features that are illustrated in FIG. 11 pertain to the width of the systolic and/or diastolic portions of the HRW curve at various "heights," which are indicated by a percentage of the maximum amplitude. For example, the SW50 feature is the width of the systolic portion of the HRW curve at a "height" of 50% of the maximum amplitude. In some implementations, the HRW features used for blood pressure estimation may include some or all of the SW10, SW25, SW33, SW50, SW66, SW75, DW10, DW25, DW33, DW50, DW66 and DW75 HRW features. In other implementations, additional HRW features may be used for blood pressure estimation. Such additional HRW features may, in some instances, include the sum and ratio of the SW and DW at one or more "heights," e.g., (DW75+SW75), DW75/SW75, (DW66+SW66), DW66/SW66, (DW50+SW50), DW50/SW50, (DW33+SW33), DW33/SW33, (DW25+SW25), DW25/SW25 and/or (DW10+SW10), DW10/SW10. Other implementations may use yet other HRW features for blood pressure estimation. Such additional HRW features may, in some instances, include sums, differences, ratios and/or other operations based on more than one "height," such as (DW75+SW75)/(DW50+SW50), (DW50+SW50/(DW10+SW10), etc.

Figure 12:
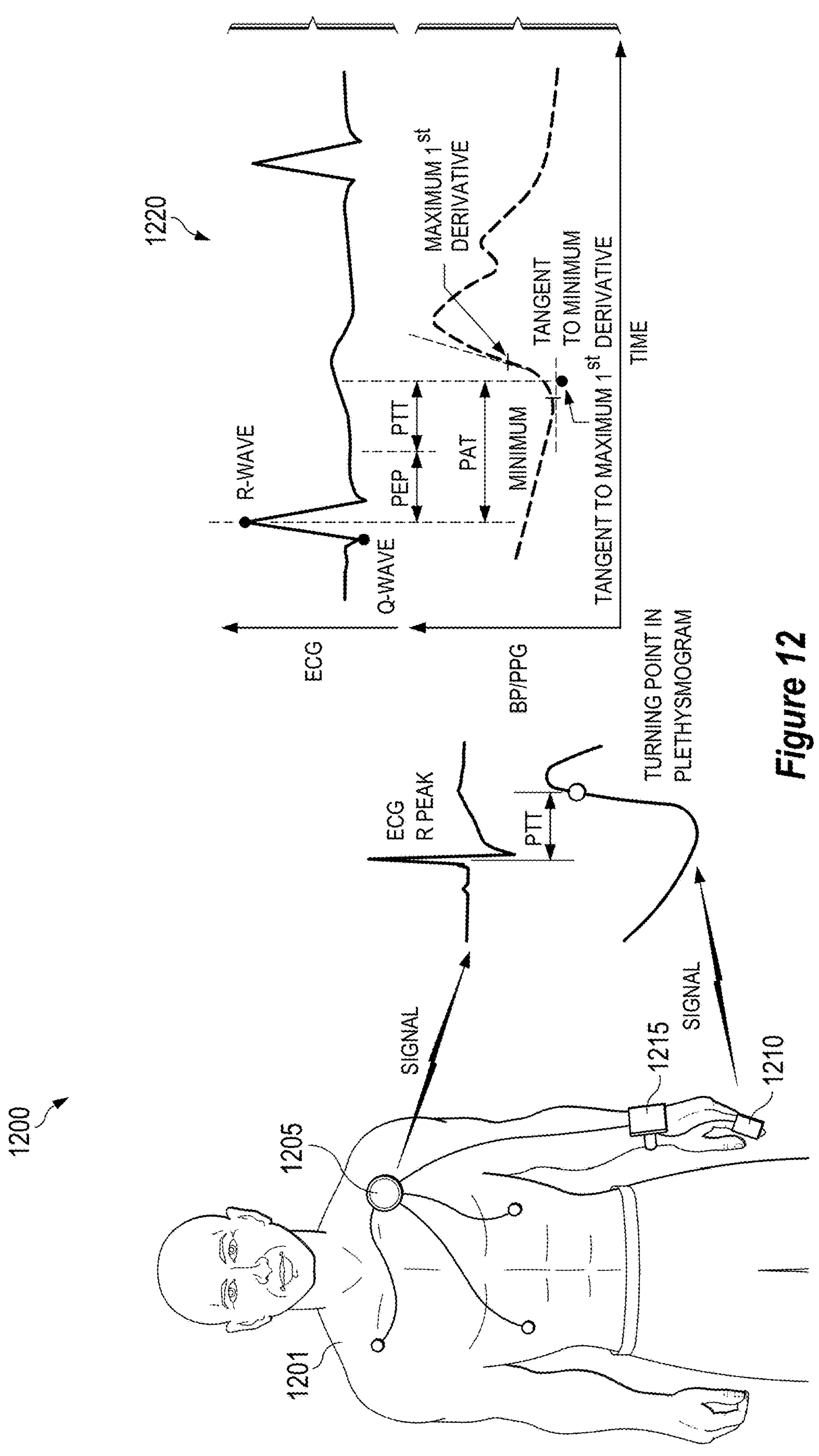
FIG. 12 shows examples of devices that may be used in a system for estimating blood pressure based, at least in part, on pulse transit time (PTT).

FIG. 12 shows examples of devices that may be used in a system for estimating blood pressure based, at least in part, on pulse transit time (PTT). As with other figures provided herein, the numbers, types and arrangements of elements are merely presented by way of example. According to this example, the system 1200 includes at least two sensors. In this example, the system 1200 includes at least an electrocardiogram sensor 1205 and a device 1210 that is configured to be mounted on a finger of the person 1201. In this example, the device 1210 is, or includes, an apparatus configured to perform at least some PAPG methods disclosed herein. For example, the device 1210 may be, or may include, the apparatus 300 of FIG. 3 or a similar apparatus.

As noted in the graph 1220, the PAT includes two components, the pre-ejection period (PEP, the time needed to convert the electrical signal into a mechanical pumping force and isovolumetric contraction to open the aortic valves) and the PTT. The starting time for the PAT can be estimated based on the QRS complex—an electrical signal characteristic of the electrical stimulation of the heart ventricles. As shown by the graph 1220, in this example the beginning of a pulse arrival time (PAT) may be calculated according to an R-Wave peak measured by the electrocardiogram sensor 1205 and the end of the PAT may be detected via analysis of signals provided by the device 1210. In this example, the end of the PAT is assumed to correspond with an intersection between a tangent to a local minimum value detected by the device 1210 and a tangent to a maximum slope/first derivative of the sensor signals after the time of the minimum value.

There are many known algorithms for blood pressure estimation based on the PTT and/or the PAT, some of which are summarized in Table 1 and described in the corresponding text on pages 5-10 of Sharma, M., et al., Cuff-Less and Continuous Blood Pressure Monitoring: a Methodological Review ("Sharma"), in Multidisciplinary Digital Publishing Institute (MDPI) Technologies 2017, 5, 21, both of which are hereby incorporated by reference.

Some previously-disclosed methods have involved calculating blood pressure according to one or more of the equations shown in Table 1 of Sharma, or other known equations, based on a PTT and/or PAT measured by a sensor system that includes a PPG sensor. As noted above, some disclosed PAPG-based implementations are configured to distinguish artery HRWs from other HRWs. Such implementations may provide more accurate measurements of the PTT and/or PAT, relative to those measured by a PPG sensor. Therefore, disclosed PAPG-based implementations may provide more accurate blood pressure estimations, even when the blood pressure estimations are based on previously-known formulae.

Other implementations of the system 1200 may not include the electrocardiogram sensor 1205. In some such implementations, the device 1215, which is configured to be mounted on a wrist of the person 1201, may be, or may include, an apparatus configured to perform at least some PAPG methods disclosed herein. For example, the device 1215 may be, or may include, the apparatus 200 of FIG. 2 or a similar apparatus. According to some such examples, the device 1215 may include a light source system and two or more ultrasonic receivers. One example is described below with reference to FIG. 14A. In some examples, the device 1215 may include an array of ultrasonic receivers.

In some implementations of the system 1200 that do not include the electrocardiogram sensor 1205, the device 1210 may include a light source system and two or more ultrasonic receivers. One example is described below with reference to FIG. 14B.

Figure 13:
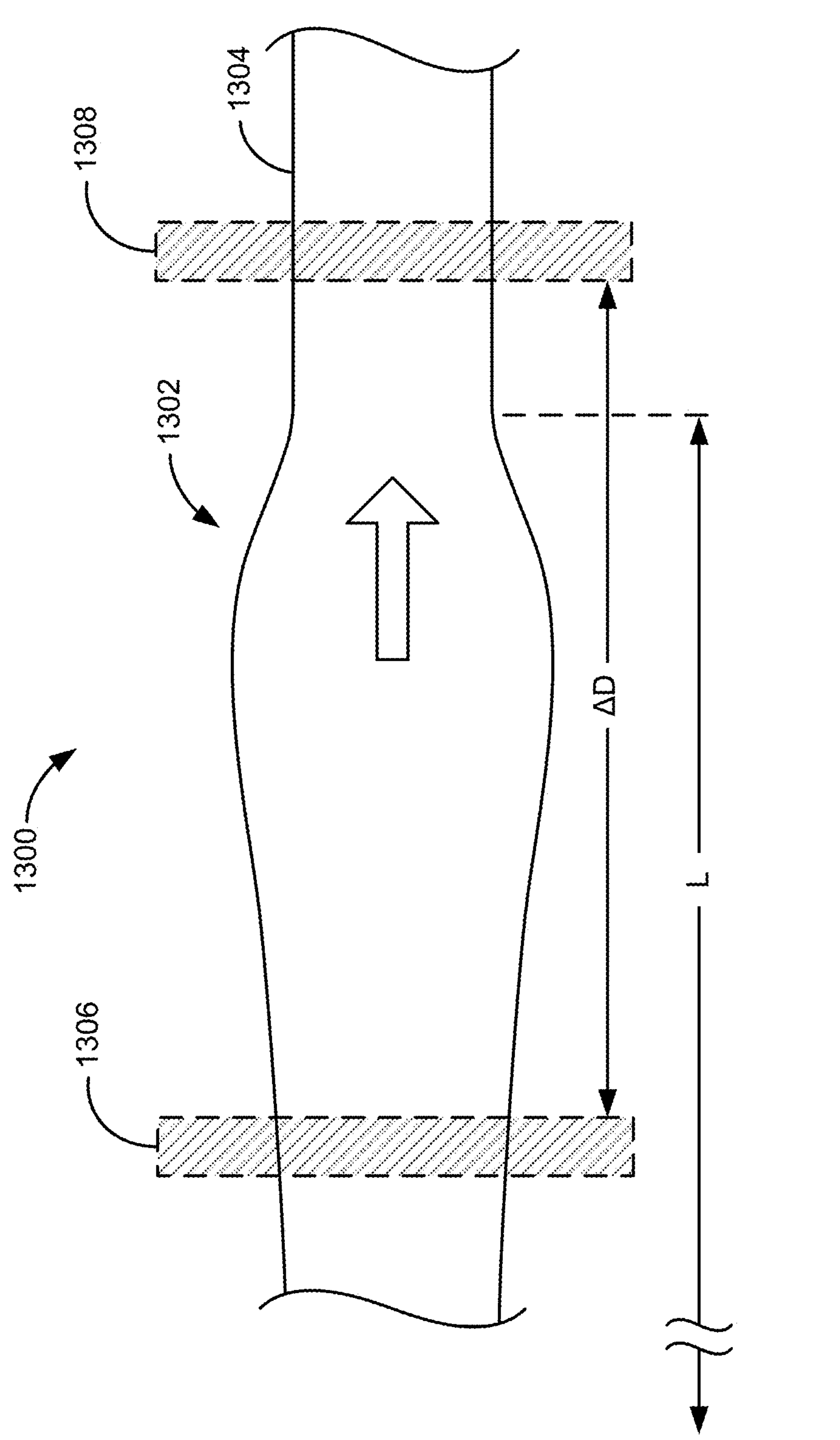
FIG. 13 shows a cross-sectional side view of a diagrammatic representation of a portion of an artery through which a pulse is propagating.

FIG. 13 shows a cross-sectional side view of a diagrammatic representation of a portion of an artery 1300 through which a pulse 1302 is propagating. The block arrow in FIG. 13 shows the direction of blood flow and pulse propagation. As diagrammatically shown, the propagating pulse 1302 causes strain in the arterial walls 1304, which is manifested in the form of an enlargement in the diameter (and consequently the cross-sectional area) of the arterial walls-referred to as "distension." The spatial length L of an actual propagating pulse along an artery (along the direction of blood flow) is typically comparable to the length of a limb, such as the distance from a subject's shoulder to the subject's wrist or finger, and is generally less than one meter (m). However, the length L of a propagating pulse can vary considerably from subject to subject, and for a given subject, can vary significantly over durations of time depending on various factors. The spatial length L of a pulse will generally decrease with increasing distance from the heart until the pulse reaches capillaries.

As described above, some particular implementations relate to devices, systems and methods for estimating blood pressure or other cardiovascular characteristics based on estimates of an arterial distension waveform. The terms "estimating," "measuring," "calculating," "inferring," "deducing," "evaluating," "determining" and "monitoring" may be used interchangeably herein where appropriate unless otherwise indicated. Similarly, derivations from the roots of these terms also are used interchangeably where appropriate; for example, the terms "estimate," "measurement," "calculation," "inference" and "determination" also are used interchangeably herein. In some implementations, the pulse wave velocity (PWV) of a propagating pulse may be estimated by measuring the pulse transit time (PTT) of the pulse as it propagates from a first physical location along an artery to another more distal second physical location along the artery. It will be appreciated that this PTT is different from the PTT that is described above with reference to FIG. 15. However, either version of the PTT may be used for the purpose of blood pressure estimation. Assuming that the physical distance AD between the first and the second physical locations is ascertainable, the PWV can be estimated as the quotient of the physical spatial distance AD traveled by the pulse divided by the time (PTT) the pulse takes in traversing the physical spatial distance AD. Generally, a first sensor positioned at the first physical location is used to determine a starting time (also referred to herein as a "first temporal location") at which point the pulse arrives at or propagates through the first physical location. A second sensor at the second physical location is used to determine an ending time (also referred to herein as a "second temporal location") at which point the pulse arrives at or propagates through the second physical location and continues through the remainder of the arterial branch. In such examples, the PTT represents the temporal distance (or time difference) between the first and the second temporal locations (the starting and the ending times).

The fact that measurements of the arterial distension waveform are performed at two different physical locations implies that the estimated PWV inevitably represents an average over the entire path distance AD through which the pulse propagates between the first physical location and the second physical location. More specifically, the PWV generally depends on a number of factors including the density of the blood p, the stiffness E of the arterial wall (or inversely the elasticity), the arterial diameter, the thickness of the arterial wall, and the blood pressure. Because both the arterial wall elasticity and baseline resting diameter (for example, the diameter at the end of the ventricular diastole period) vary significantly throughout the arterial system, PWV estimates obtained from PTT measurements are inherently average values (averaged over the entire path length AD between the two locations where the measurements are performed).

In traditional methods for obtaining PWV, the starting time of the pulse has been obtained at the heart using an electrocardiogram (ECG) sensor, which detects electrical signals from the heart. For example, the starting time can be estimated based on the QRS complex—an electrical signal characteristic of the electrical stimulation of the heart ventricles. In such approaches, the ending time of the pulse is typically obtained using a different sensor positioned at a second location (for example, a finger). As a person having ordinary skill in the art will appreciate, there are numerous arterial discontinuities, branches, and variations along the entire path length from the heart to the finger. The PWV can change by as much as or more than an order of magnitude along various stretches of the entire path length from the heart to the finger. As such, PWV estimates based on such long path lengths are unreliable.

In various implementations described herein, PTT estimates are obtained based on measurements (also referred to as "arterial distension data" or more generally as "sensor data") associated with an arterial distension signal obtained by each of a first arterial distension sensor 1306 and a second arterial distension sensor 1308 proximate first and second physical locations, respectively, along an artery of interest. In some particular implementations, the first arterial distension sensor 1306 and the second arterial distension sensor 1308 are advantageously positioned proximate first and second physical locations between which arterial properties of the artery of interest, such as wall elasticity and diameter, can be considered or assumed to be relatively constant. In this way, the PWV calculated based on the PTT estimate is more representative of the actual PWV along the particular segment of the artery. In turn, the blood pressure P estimated based on the PWV is more representative of the true blood pressure. In some implementations, the magnitude of the distance AD of separation between the first arterial distension sensor 1306 and the second arterial distension sensor 1308 (and consequently the distance between the first and the second locations along the artery) can be in the range of about 1 centimeter (cm) to tens of centimeters-long enough to distinguish the arrival of the pulse at the first physical location from the arrival of the pulse at the second physical location, but close enough to provide sufficient assurance of arterial consistency. In some specific implementations, the distance AD between the first and the second arterial distension sensors 1306 and 1308 can be in the range of about 1 cm to about 30 cm, and in some implementations, less than or equal to about 20 cm, and in some implementations, less than or equal to about 10 cm, and in some specific implementations less than or equal to about 5 cm. In some other implementations, the distance AD between the first and the second arterial distension sensors 1306 and 1308 can be less than or equal to 1 cm, for example, about 0.1 cm, about 0.25 cm, about 0.5 cm or about 0.75 cm. By way of reference, a typical PWV can be about 15 meters per second (m/s). Using an ambulatory monitoring device in which the first and the second arterial distension sensors 1306 and 1308 are separated by a distance of about 5 cm, and assuming a PWV of about 15 m/s implies a PTT of approximately 3.3 milliseconds (ms).

The value of the magnitude of the distance AD between the first and the second arterial distension sensors 1306 and 1308, respectively, can be preprogrammed into a memory within a monitoring device that incorporates the sensors (for example, such as a memory of, or a memory configured for communication with, the control system 306 that is described above with reference to FIG. 3). As will be appreciated by a person of ordinary skill in the art, the spatial length L of a pulse can be greater than the distance AD from the first arterial distension sensor 1306 to the second arterial distension sensor 1308 in such implementations. As such, although the diagrammatic pulse 1302 shown in FIG. 13 is shown as having a spatial length L comparable to the distance between the first arterial distension sensor 1306 and the second arterial distension sensor 1308, in actuality each pulse can typically have a spatial length L that is greater and even much greater than (for example, about an order of magnitude or more than) the distance AD between the first and the second arterial distension sensors 1306 and 1308.

Sensing Architecture and Topology

In some implementations of the ambulatory monitoring devices disclosed herein, both the first arterial distension sensor 1306 and the second arterial distension sensor 1308 are sensors of the same sensor type. In some such implementations, the first arterial distension sensor 1306 and the second arterial distension sensor 1308 are identical sensors. In such implementations, each of the first arterial distension sensor 1306 and the second arterial distension sensor 1308 utilizes the same sensor technology with the same sensitivity to the arterial distension signal caused by the propagating pulses, and has the same time delays and sampling characteristics. In some implementations, each of the first arterial distension sensor 1306 and the second arterial distension sensor 1308 is configured for photoacoustic plethysmography (PAPG) sensing, e.g., as disclosed elsewhere herein. Some such implementations include a light source system and two or more ultrasonic receivers, which may be instances of the light source system 304 and the receiver system 302 of FIG. 3. In some implementations, each of the first arterial distension sensor 1306 and the second arterial distension sensor 1308 is configured for ultrasound sensing via the transmission of ultrasonic signals and the receipt of corresponding reflections. In some alternative implementations, each of the first arterial distension sensor 1306 and the second arterial distension sensor 1308 may be configured for impedance plethysmography (IPG) sensing, also referred to in biomedical contexts as bioimpedance sensing. In various implementations, whatever types of sensors are utilized, each of the first and the second arterial distension sensors 1306 and 1308 broadly functions to capture and provide arterial distension data indicative of an arterial distension signal resulting from the propagation of pulses through a portion of the artery proximate to which the respective sensor is positioned. For example, the arterial distension data can be provided from the sensor to a processor in the form of voltage signal generated or received by the sensor based on an ultrasonic signal or an impedance signal sensed by the respective sensor.

As described above, during the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

In the context of bioimpedance sensing (or impedance plethysmography), the blood in the arteries has a greater electrical conductivity than that of the surrounding or adjacent skin, muscle, fat, tendons, ligaments, bone, lymph or other tissues. The susceptance (and thus the permittivity) of blood also is different from the susceptances (and permittivities) of the other types of surrounding or nearby tissues. As a pulse propagates through a particular location, the corresponding increase in the volume of blood results in an increase in the electrical conductivity at the particular location (and more generally an increase in the admittance, or equivalently a decrease in the impedance). Conversely, during the diastolic phase of the cardiac cycle, the corresponding decrease in the volume of blood results in an increase in the electrical resistivity at the particular location (and more generally an increase in the impedance, or equivalently a decrease in the admittance).

A bioimpedance sensor generally functions by applying an electrical excitation signal at an excitation carrier frequency to a region of interest via two or more input electrodes, and detecting an output signal (or output signals) via two or more output electrodes. In some more specific implementations, the electrical excitation signal is an electrical current signal injected into the region of interest via the input electrodes. In some such implementations, the output signal is a voltage signal representative of an electrical voltage response of the tissues in the region of interest to the applied excitation signal. The detected voltage response signal is influenced by the different, and in some instances time-varying, electrical properties of the various tissues through which the injected excitation current signal is passed. In some implementations in which the bioimpedance sensor is operable to monitor blood pressure, heartrate or other cardiovascular characteristics, the detected voltage response signal is amplitude- and phase-modulated by the time-varying impedance (or inversely the admittance) of the underlying arteries, which fluctuates synchronously with the user's heartbeat as described above. To determine various biological characteristics, information in the detected voltage response signal is generally demodulated from the excitation carrier frequency component using various analog or digital signal processing circuits, which can include both passive and active components.

In some examples incorporating ultrasound sensors, measurements of arterial distension may involve directing ultrasonic waves into a limb towards an artery, for example, via one or more ultrasound transducers. Such ultrasound sensors also are configured to receive reflected waves that are based, at least in part, on the directed waves. The reflected waves may include scattered waves, specularly reflected waves, or both scattered waves and specularly reflected waves. The reflected waves provide information about the arterial walls, and thus the arterial distension.

In some implementations, regardless of the type of sensors utilized for the first arterial distension sensor 1306 and the second arterial distension sensor 1308, both the first arterial distension sensor 1306 and the second arterial distension sensor 1308 can be arranged, assembled or otherwise included within a single housing of a single ambulatory monitoring device. As described above, the housing and other components of the monitoring device can be configured such that when the monitoring device is affixed or otherwise physically coupled to a subject, both the first arterial distension sensor 1306 and the second arterial distension sensor 1308 are in contact with or in close proximity to the skin of the user at first and second locations, respectively, separated by a distance AD, and in some implementations, along a stretch of the artery between which various arterial properties can be assumed to be relatively constant. In various implementations, the housing of the ambulatory monitoring device is a wearable housing or is incorporated into or integrated with a wearable housing. In some specific implementations, the wearable housing includes (or is connected with) a physical coupling mechanism for removable non-invasive attachment to the user. The housing can be formed using any of a variety of suitable manufacturing processes, including injection molding and vacuum forming, among others. In addition, the housing can be made from any of a variety of suitable materials, including, but not limited to, plastic, metal, glass, rubber and ceramic, or combinations of these or other materials. In particular implementations, the housing and coupling mechanism enable full ambulatory use. In other words, some implementations of the wearable monitoring devices described herein are non-invasive, not physically-inhibiting and generally do not restrict the free uninhibited motion of a subject's arms or legs, enabling continuous or periodic monitoring of cardiovascular characteristics such as blood pressure even as the subject is mobile or otherwise engaged in a physical activity. As such, the ambulatory monitoring device facilitates and enables long-term wearing and monitoring (for example, over days, weeks or a month or more without interruption) of one or more biological characteristics of interest to obtain a better picture of such characteristics over extended durations of time, and generally, a better picture of the user's health.

Figure 14A:
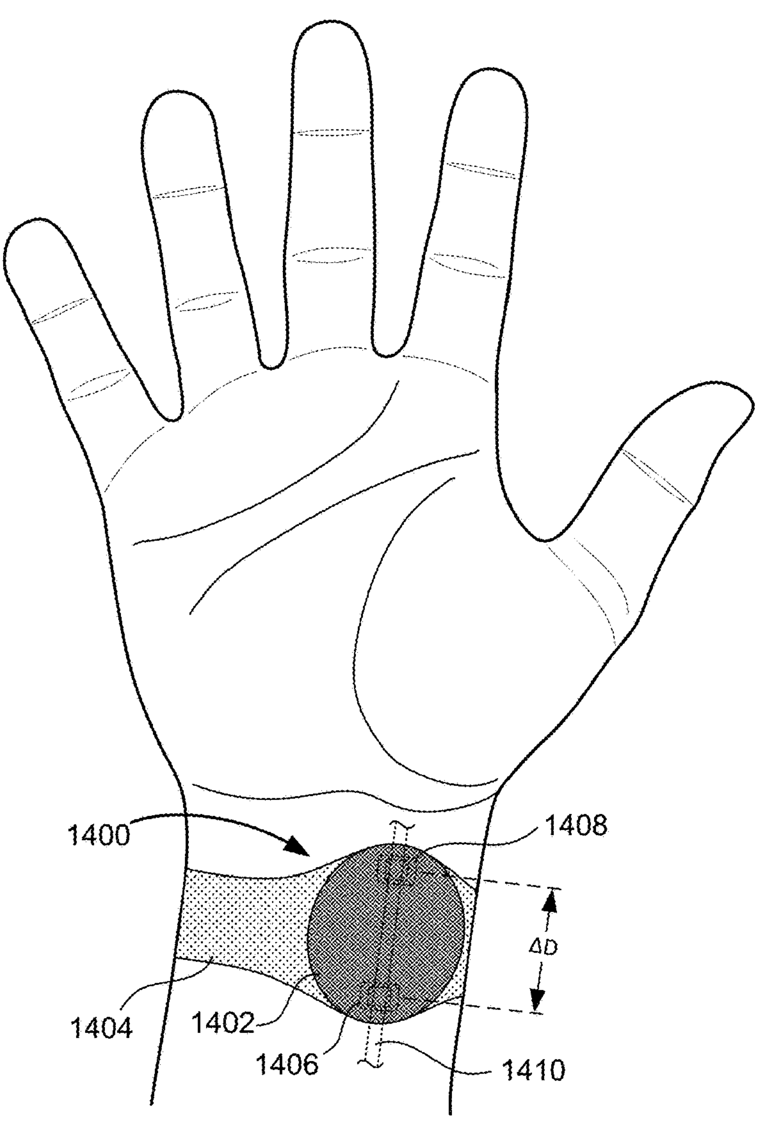
FIG. 14A shows an example ambulatory monitoring device designed to be worn around a wrist according to some implementations.

In some implementations, the ambulatory monitoring device can be positioned around a wrist of a user with a strap or band, similar to a watch or fitness/activity tracker. FIG. 14A shows an example ambulatory monitoring device 1400 designed to be worn around a wrist according to some implementations. In the illustrated example, the monitoring device 1400 includes a housing 1402 integrally formed with, coupled with or otherwise integrated with a wristband 1404. The first and the second arterial distension sensors 1406 and 1408 may, in some instances, each include an instance of the ultrasonic receiver system 302 and a portion of the light source system 304 that are described above with reference to FIG. 3. In this example, the ambulatory monitoring device 1400 is coupled around the wrist such that the first and the second arterial distension sensors 1406 and 1408 within the housing 1402 are each positioned along a segment of the radial artery 1410 (note that the sensors are generally hidden from view from the external or outer surface of the housing facing the subject while the monitoring device is coupled with the subject, but exposed on an inner surface of the housing to enable the sensors to obtain measurements through the subject's skin from the underlying artery). Also as shown, the first and the second arterial distension sensors 1406 and 1408 are separated by a fixed distance AD. In some other implementations, the ambulatory monitoring device 1400 can similarly be designed or adapted for positioning around a forearm, an upper arm, an ankle, a lower leg, an upper leg, or a finger (all of which are hereinafter referred to as "limbs") using a strap or band.

Figure 14B:
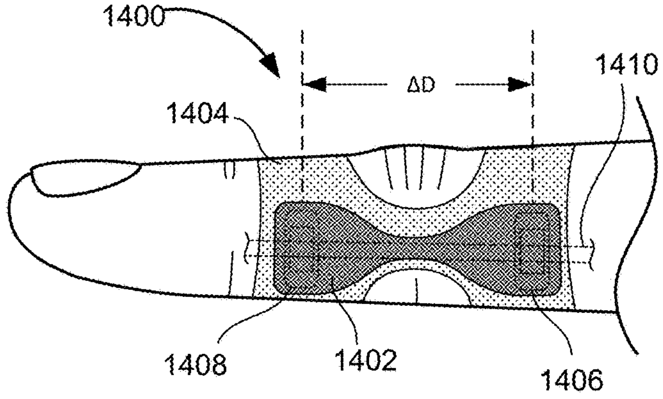
FIG. 14B shows an example ambulatory monitoring device designed to be worn on a finger according to some implementations.

FIG. 14B shows an example ambulatory monitoring device 1400 designed to be worn on a finger according to some implementations. The first and the second arterial distension sensors 1406 and 1408 may, in some instances, each include an instance of the ultrasonic receiver 302 and a portion of the light source system 304 that are described above with reference to FIG. 3.

In some other implementations, the ambulatory monitoring devices disclosed herein can be positioned on a region of interest of the user without the use of a strap or band. For example, the first and the second arterial distension sensors 1406 and 1408 and other components of the monitoring device can be enclosed in a housing that is secured to the skin of a region of interest of the user using an adhesive or other suitable attachment mechanism (an example of a "patch" monitoring device).

Figure 14C:
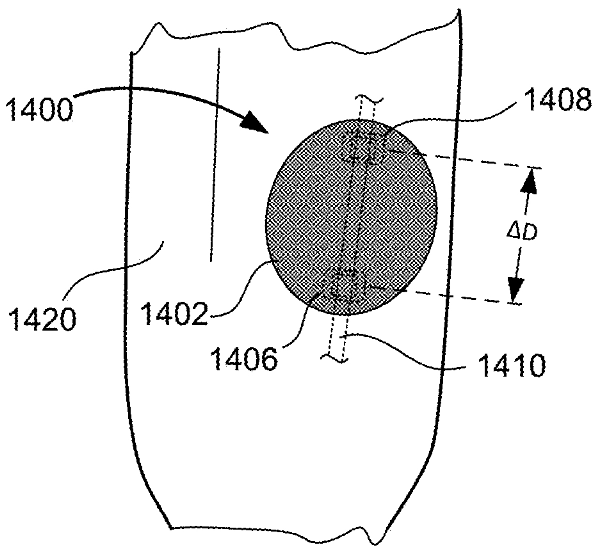
FIG. 14C shows an example ambulatory monitoring device designed to reside on an earbud according to some implementations.

FIG. 14C shows an example ambulatory monitoring device 1400 designed to reside on an earbud according to some implementations. According to this example, the ambulatory monitoring device 1400 is coupled to the housing of an earbud 1420. The first and second arterial distension sensors 1406 and 1408 may, in some instances, each include an instance of the ultrasonic receiver 302 and a portion of the light source system 304 that are described above with reference to FIG. 3.

Implementation examples are described in the following numbered clauses:

1. An apparatus, including: a platen; a light source system configured for providing light to a target object on an outer surface of the platen; an ultrasonic receiver system configured to receive ultrasonic waves generated by the target object responsive to the light from the light source system, the ultrasonic receiver system including an array of ultrasonic receiver elements; and a control system configured to: receive ultrasonic receiver signals from each of a plurality of ultrasonic receiver elements in the array; apply a receiver-side beamforming process to the ultrasonic receiver signals, to produce a beamformed ultrasonic receiver image; and detect a blood vessel within the targe object based, at least in part, on the beamformed ultrasonic receiver image.
2. The apparatus of clause 1, where the control system is configured to detect the blood vessel within the targe object based, at least in part, on the ultrasonic receiver signals.
3. The apparatus of clause 1 or clause 2, where the control system is further configured to estimate one or more blood vessel features based, at least in part, on the beamformed ultrasonic receiver image.
4. The apparatus of clause 3, where the one or more blood vessel features include blood vessel diameter, blood vessel area, blood vessel profile, blood vessel distention, volumetric flow, pulse wave velocity, blood vessel wall thickness, or combinations thereof.
5. The apparatus of clause 3 or clause 4, where the control system is further configured to estimate blood pressure based, at least in part, on the one or more blood vessel features.
6. The apparatus of any one of clauses 1-5, where the light source system includes an array of light sources.
7. The apparatus of any one of clauses 1-6, where the apparatus is configured to be worn by, or attached to, a person.
8. The apparatus of clause 7, where the array of ultrasonic receiver elements includes a linear array of ultrasonic receiver elements arranged along an array axis that is configured to extend along the blood vessel and where the array axis is within plus or minus 45 degrees of a blood vessel axis.
9. The apparatus of clause 7, where the array of ultrasonic receiver elements includes a linear array of ultrasonic receiver elements arranged along an array axis that is configured to extend across the blood vessel.
10. The apparatus of any one of clauses 1-9, where the array of ultrasonic receiver elements includes a linear array of ultrasonic receiver elements having a pitch between adjacent ultrasonic receiver elements that is equal to a wavelength corresponding to a peak frequency of ultrasonic waves generated by the target object responsive to the light from the light source system.
11. The apparatus of any one of clauses 1-10, where the array of ultrasonic receiver elements includes a phased array of ultrasonic receiver elements having a pitch between adjacent ultrasonic receiver elements that is equal to a multiple of a half wavelength corresponding to a peak frequency of ultrasonic waves generated by the target object responsive to the light from the light source system.
12. The apparatus of any one of clauses 1-11, where the array of ultrasonic receiver elements includes a two-dimensional array of ultrasonic receiver elements.
13. The apparatus of any one of clauses 1-12, where the array of ultrasonic receiver elements is, or includes, an array of electrodes arranged on a piezoelectric layer.
14. The apparatus of clause 13, where the piezoelectric layer is, or includes, lead zirconate titanate (PZT) or a piezoelectric composite.
15. The apparatus of clause 1, where the receiver-side beamforming process is, or includes, a delay-and-sum beamforming process.
16. An apparatus, including: a platen; a light source system configured for providing light to a target object on an outer surface of the platen; an ultrasonic receiver system configured to receive ultrasonic waves generated by the target object responsive to the light from the light source system, the ultrasonic receiver system including an array of ultrasonic receiver elements; and control means for: receiving ultrasonic receiver signals from each of a plurality of ultrasonic receiver elements in the array; applying a receiver-side beamforming process to the ultrasonic receiver signals, to produce a beamformed ultrasonic receiver image; and detecting a blood vessel within the targe object based, at least in part, on the beamformed ultrasonic receiver image.
17. The apparatus of clause 16, where the control means includes means for detecting the blood vessel within the targe object based, at least in part, on the ultrasonic receiver signals.
18. The apparatus of clause 16, where the control means includes means for estimating one or more blood vessel features based, at least in part, on the beamformed ultrasonic receiver image.
19. The apparatus of clause 18, where the one or more blood vessel features include blood vessel diameter, blood vessel distention, volumetric flow, pulse wave velocity, blood vessel wall thickness, or combinations thereof.
20. The apparatus of clause 18, where the control means includes means for estimating blood pressure based, at least in part, on the one or more blood vessel features.
21. A method, including: controlling, by a control system, a light source system to provide light to a target object on an outer surface of a platen; receiving, by the control system, ultrasonic receiver signals from each of a plurality of ultrasonic receiver elements in an array of ultrasonic receiver elements, the ultrasonic receiver signals corresponding to ultrasonic waves generated by the target object responsive to the light from the light source system; applying, by the control system, a receiver-side beamforming process to the ultrasonic receiver signals, to produce a beamformed ultrasonic receiver image; and detecting, by the control system, a blood vessel within the targe object based, at least in part, on the beamformed ultrasonic receiver image.
22. The method of clause 21, further including detecting the blood vessel within the target object based, at least in part, on the ultrasonic receiver signals.

23. The method of clause 21 or clause 22, further including estimating one or more blood vessel features based, at least in part, on the beamformed ultrasonic receiver image.
24. The method of clause 23, where the one or more blood vessel features include blood vessel diameter, blood vessel area, blood vessel profile, blood vessel distention, volumetric flow, pulse wave velocity, blood vessel wall thickness, or combinations thereof.
25. The method of clause 23 or clause 24, further including estimating blood pressure based, at least in part, on the one or more blood vessel features.
26. The method of any one of clauses 21-25, where the receiver-side beamforming process includes a delay-and-sum beamforming process.
27. One or more non-transitory media having instructions for performing a method stored thereon, the method including: controlling a light source system to provide light to a target object on an outer surface of a platen; receiving, by a control system, ultrasonic receiver signals from each of a plurality of ultrasonic receiver elements in an array of ultrasonic receiver elements, the ultrasonic receiver signals corresponding to ultrasonic waves generated by the target object responsive to the light from the light source system; applying a receiver-side beamforming process to the ultrasonic receiver signals, to produce a beamformed ultrasonic receiver image; and detecting a blood vessel within the targe object based, at least in part, on the beamformed ultrasonic receiver image.
28. The one or more non-transitory media of clause 27, where the method further includes detecting the blood vessel within the target object based, at least in part, on the ultrasonic receiver signals.
29. The one or more non-transitory media of clause 27 or clause 28, where the method further includes estimating one or more blood vessel features based, at least in part, on the beamformed ultrasonic receiver image.
30. The one or more non-transitory media of clause 29, where the one or more blood vessel features include blood vessel diameter, blood vessel area, blood vessel profile, blood vessel distention, volumetric flow, pulse wave velocity, blood vessel wall thickness, or combinations thereof.
31. The one or more non-transitory media of clause 29 or clause 30, where the method further includes estimating blood pressure based, at least in part, on the one or more blood vessel features.
32. The one or more non-transitory media of any one of clauses 27-31, where the receiver-side beamforming process includes a delay-and-sum beamforming process.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD™), floppy disk, and Blu-ray Disc® where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

Various modifications to the implementations described in this disclosure may be readily apparent to those skilled in the art, and the generic principles defined herein may be applied to other implementations without departing from the spirit or scope of this disclosure. Thus, the following claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

What is claimed is:

1. An apparatus, comprising:

a platen;

a light source system configured for providing light to a target object on an outer surface of the platen;

an ultrasonic receiver system configured to receive ultrasonic waves generated by the target object responsive to the light from the light source system, the ultrasonic receiver system including an array of ultrasonic receiver elements, wherein the array of ultrasonic receiver elements includes a linear array of ultrasonic receiver elements having a pitch between adjacent ultrasonic receiver elements that is equal to a wavelength corresponding to a peak frequency of ultrasonic waves generated by the target object responsive to the light from the light source system; and a control system configured to:

receive ultrasonic receiver signals from each of a plurality of ultrasonic receiver elements in the array;

apply a receiver-side beamforming process to the ultrasonic receiver signals, to produce a beamformed ultrasonic receiver image; and detect a blood vessel within the target object based, at least in part, on the beamformed ultrasonic receiver image.

2. The apparatus of claim 1, wherein the control system is configured to detect the blood vessel within the target object based, at least in part, on the ultrasonic receiver signals.

3. The apparatus of claim 1, wherein the control system is further configured to estimate one or more blood vessel features based, at least in part, on the beamformed ultrasonic receiver image.

4. The apparatus of claim 3, wherein the one or more blood vessel features include blood vessel diameter, blood vessel area, blood vessel profile, blood vessel distention, volumetric flow, pulse wave velocity, blood vessel wall thickness, or combinations thereof.

5. The apparatus of claim 3, wherein the control system is further configured to estimate blood pressure based, at least in part, on the one or more blood vessel features.

6. The apparatus of claim 1, wherein the light source system comprises an array of light sources.

7. The apparatus of claim 1, wherein the apparatus is configured to be worn by, or attached to, a person.

8. The apparatus of claim 7, wherein the array of ultrasonic receiver elements includes a linear array of ultrasonic receiver elements arranged along an array axis that is configured to extend along the blood vessel and wherein the array axis is within plus or minus 45 degrees of a blood vessel axis.

9. The apparatus of claim 7, wherein the array of ultrasonic receiver elements includes a linear array of ultrasonic receiver elements arranged along an array axis that is configured to extend across the blood vessel.

10. The apparatus of claim 1, wherein the array of ultrasonic receiver elements comprises a two-dimensional array of ultrasonic receiver elements.

11. The apparatus of claim 1, wherein the array of ultrasonic receiver elements comprises an array of electrodes arranged on a piezoelectric layer.

12. The apparatus of claim 11, wherein the piezoelectric layer comprises lead zirconate titanate (PZT) or a piezoelectric composite.

13. The apparatus of claim 1, wherein the receiver-side beamforming process comprises a delay-and-sum beamforming process.

14. A wearable apparatus, comprising:

a platen;

a light source system configured for providing light to a target object on an outer surface of the platen;

an ultrasonic receiver system configured to receive ultrasonic waves generated by the target object responsive to the light from the light source system, the ultrasonic receiver system including an array of ultrasonic receiver elements, wherein the array of ultrasonic receiver elements includes a linear array of ultrasonic receiver elements having a pitch between adjacent ultrasonic receiver elements that is equal to a wavelength corresponding to a peak frequency of ultrasonic waves generated by the target object responsive to the light from the light source system;

control means for:

receiving ultrasonic receiver signals from each of a plurality of ultrasonic receiver elements in the array;

applying a receiver-side beamforming process to the ultrasonic receiver signals, to produce a beamformed ultrasonic receiver image; and detecting a blood vessel within the target object based, at least in part, on the beamformed ultrasonic receiver image; and a wearable housing, wherein the platen, the light source system, the ultrasonic receiver system and the control means are included within, or attached to, the wearable housing.

15. The apparatus of claim 14, wherein the control means includes means for detecting the blood vessel within the target object based, at least in part, on the ultrasonic receiver signals.

16. The apparatus of claim 14, wherein the control means includes means for estimating one or more blood vessel features based, at least in part, on the beamformed ultrasonic receiver image.

17. The apparatus of claim 16, wherein the one or more blood vessel features include blood vessel diameter, blood vessel distention, volumetric flow, pulse wave velocity, blood vessel wall thickness, or combinations thereof.

18. The apparatus of claim 16, wherein the control means includes means for estimating blood pressure based, at least in part, on the one or more blood vessel features.

19. A method, comprising:

controlling, by a control system, a light source system to provide light to a target object on an outer surface of a platen;

receiving, by the control system, ultrasonic receiver signals from each of a plurality of ultrasonic receiver elements in an array of ultrasonic receiver elements, the array of ultrasonic receiver elements including a linear array of ultrasonic receiver elements having a pitch between adjacent ultrasonic receiver elements that is equal to a wavelength corresponding to a peak frequency of ultrasonic waves generated by the target object responsive to the light from the light source system, the ultrasonic receiver signals corresponding to ultrasonic waves generated by the target object responsive to the light from the light source system;

applying, by the control system, a receiver-side beamforming process to the ultrasonic receiver signals, to produce a beamformed ultrasonic receiver image; and detecting, by the control system, a blood vessel within the target object based, at least in part, on the beamformed ultrasonic receiver image.

20. The method of claim 19, further comprising detecting the blood vessel within the target object based, at least in part, on the ultrasonic receiver signals.

21. The method of claim 19, further comprising estimating one or more blood vessel features based, at least in part, on the beamformed ultrasonic receiver image.

22. The method of claim 21, wherein the one or more blood vessel features include blood vessel diameter, blood vessel area, blood vessel profile, blood vessel distention, volumetric flow, pulse wave velocity, blood vessel wall thickness, or combinations thereof.

23. The method of claim 21, further comprising estimating blood pressure based, at least in part, on the one or more blood vessel features.

24. The method of claim 19, wherein the receiver-side beamforming process comprises a delay-and-sum beamforming process.

25. One or more non-transitory computer-readable media having instructions for performing a method stored thereon, the method comprising:

controlling a light source system to provide light to a target object on an outer surface of a platen;

receiving, by a control system, ultrasonic receiver signals from each of a plurality of ultrasonic receiver elements in an array of ultrasonic receiver elements, the array of ultrasonic receiver elements including a linear array of ultrasonic receiver elements having a pitch between adjacent ultrasonic receiver elements that is equal to a wavelength corresponding to a peak frequency of ultrasonic waves generated by the target object responsive to the light from the light source system, the ultrasonic receiver signals corresponding to ultrasonic waves generated by the target object responsive to the light from the light source system;

applying a receiver-side beamforming process to the ultrasonic receiver signals, to produce a beamformed ultrasonic receiver image; and detecting a blood vessel within the target object based, at least in part, on the beamformed ultrasonic receiver image.

26. The one or more non-transitory media of claim 25, wherein the method further comprises detecting the blood vessel within the target object based, at least in part, on the ultrasonic receiver signals.

27. The one or more non-transitory media of claim 25, wherein the method further comprises estimating one or more blood vessel features based, at least in part, on the beamformed ultrasonic receiver image.

28. The one or more non-transitory media of claim 27, wherein the one or more blood vessel features include blood vessel diameter, blood vessel area, blood vessel profile, blood vessel distention, volumetric flow, pulse wave velocity, blood vessel wall thickness, or combinations thereof.

29. The one or more non-transitory media of claim 27, wherein the method further comprises estimating blood pressure based, at least in part, on the one or more blood vessel features.

30. The one or more non-transitory media of claim 25, wherein the receiver-side beamforming process comprises a delay-and-sum beamforming process.

* * * * *